US008585581B2

(12) United States Patent
Narthasilpa et al.

(10) Patent No.: US 8,585,581 B2
(45) Date of Patent: Nov. 19, 2013

(54) APPARATUS, SYSTEM AND METHOD OF MINIMALLY INVASIVE REPAIR OF PELVIC ORGAN PROLAPSE

(75) Inventors: Pornpimon Narthasilpa, St. Paul, MN (US); Mark A. Moschel, New Hope, MN (US); Christopher A. Thierfelder, Minneapolis, MN (US); Julie M. Woessner, Minneapolis, MN (US); Steve Knop, Maple Grove, MN (US); Randy L. Morningstar, Brooklyn Park, MN (US); Steven B. McClurg, Roseville, MN (US); Don Wolf, Vadnais Heights, MN (US)

(73) Assignee: Coloplast A/S, Humlebaek (DK)

( * ) Notice: Subject to any disclaimer, the term of this patent is extended or adjusted under 35 U.S.C. 154(b) by 447 days.

(21) Appl. No.: 12/873,357

(22) Filed: Sep. 1, 2010

(65) Prior Publication Data
US 2011/0054249 A1 Mar. 3, 2011

Related U.S. Application Data

(60) Provisional application No. 61/238,846, filed on Sep. 1, 2009.

(51) Int. Cl.
*A61F 2/00* (2006.01)
*A61F 13/00* (2006.01)

(52) U.S. Cl.
USPC ............. 600/37; 606/151; 606/142; 623/1.11

(58) Field of Classification Search
USPC ............ 600/37, 433–435, 466, 585; 606/108, 606/151; 604/508, 523, 528; 607/122; 623/1.11
See application file for complete search history.

(56) References Cited

U.S. PATENT DOCUMENTS

| 3,470,875 | A  | * | 10/1969 | Johnson | 606/145 |
| 5,364,002 | A  | * | 11/1994 | Green et al. | 227/177.1 |
| 5,370,650 | A  | * | 12/1994 | Tovey et al. | 606/151 |
| 6,074,395 | A  | * | 6/2000  | Trott et al. | 606/104 |
| 6,267,772 | B1 | * | 7/2001  | Mulhauser et al. | 606/151 |
| 6,475,139 | B1 | * | 11/2002 | Miller | 600/135 |
| 2002/0095064 | A1 | * | 7/2002 | Beyar | 600/30 |
| 2005/0250977 | A1 | * | 11/2005 | Montpetit et al. | 600/29 |
| 2006/0004433 | A1 | * | 1/2006 | Greenberg et al. | 623/1.11 |
| 2006/0207418 | A1 | * | 9/2006 | Burke | 89/12 |
| 2006/0229596 | A1 | * | 10/2006 | Weiser et al. | 606/37 |

(Continued)

FOREIGN PATENT DOCUMENTS

| WO | 2006/005117 | 1/2006 |
| WO | 2007/101970 | 9/2007 |

(Continued)

OTHER PUBLICATIONS

Partial European search report in the related international application No. PCT/DK2010/050225, dated Dec. 13, 2011.

*Primary Examiner* — Charles A Marmor, II
*Assistant Examiner* — Eileen Foley
(74) *Attorney, Agent, or Firm* — Coloplast Corp., Coloplast A/S; Nick Baumann

(57) ABSTRACT

A system for repair of a prolapsed organ in a patient includes a support and a deployment instrument having a handle extending from a barrel and a trigger offset from the handle, the trigger is operable to advance the support out of the barrel of the deployment instrument and into the patient.

21 Claims, 23 Drawing Sheets

(56) References Cited

U.S. PATENT DOCUMENTS

| | | |
|---|---|---|
| 2007/0142846 A1* | 6/2007 | Catanese et al. .............. 606/142 |
| 2008/0027273 A1* | 1/2008 | Gutterman ...................... 600/37 |
| 2008/0039874 A1* | 2/2008 | Catanese et al. .............. 606/142 |
| 2008/0058584 A1* | 3/2008 | Hirotsuka et al. .............. 600/37 |
| 2009/0192530 A1* | 7/2009 | Adzich et al. ................. 606/151 |

FOREIGN PATENT DOCUMENTS

| | | |
|---|---|---|
| WO | 2007/146784 | 12/2007 |
| WO | 2009/005714 A2 | 1/2009 |
| WO | WO 2009005714 A2 * | 1/2009 |
| WO | 2009/016517 | 2/2009 |

\* cited by examiner

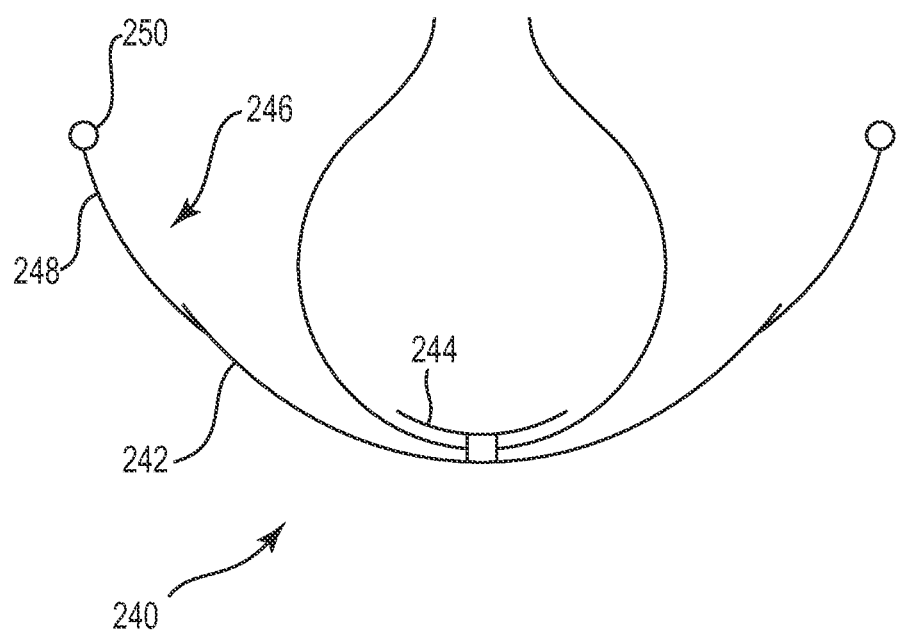
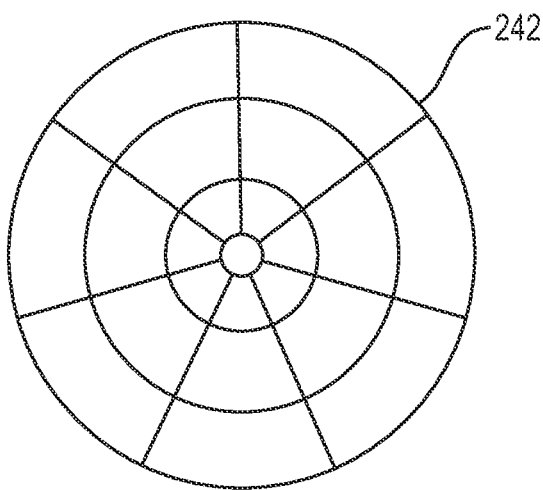
Fig. 12

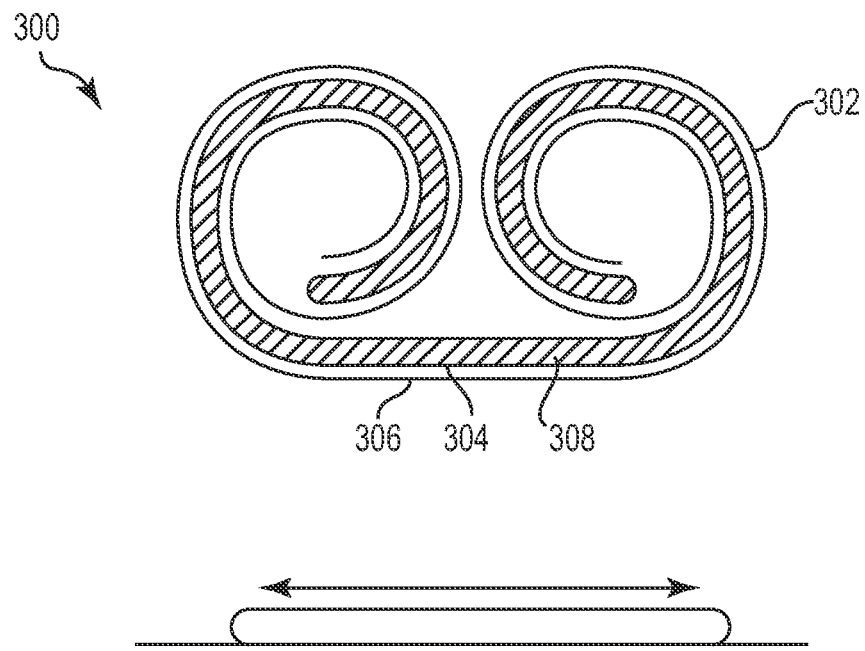
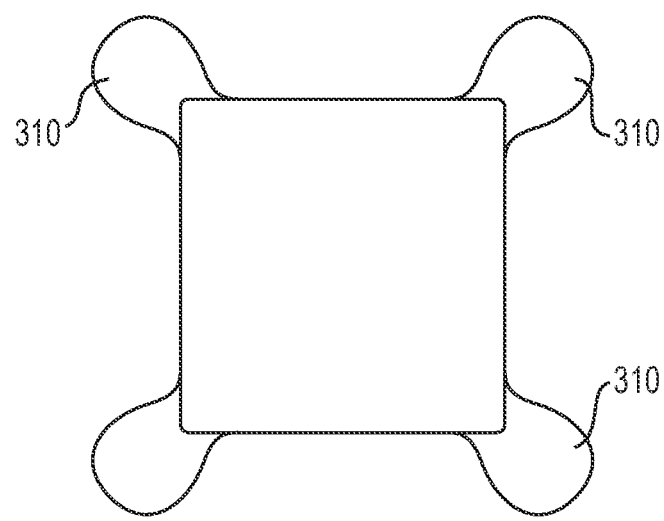
Fig. 16

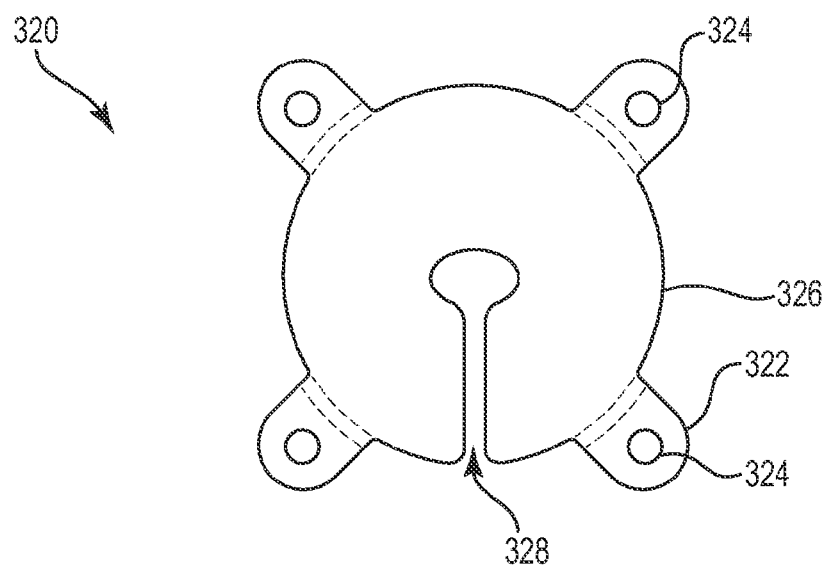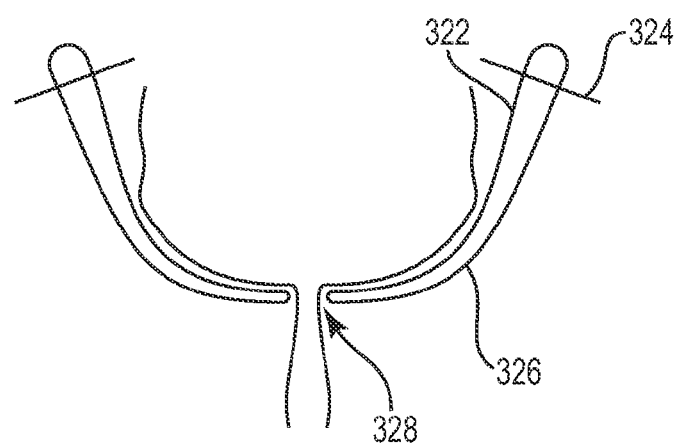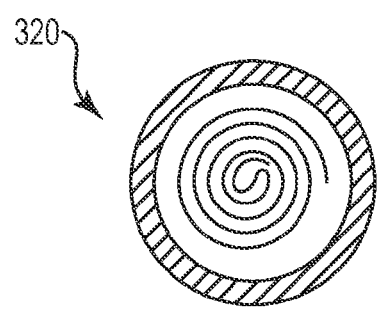
Fig. 17

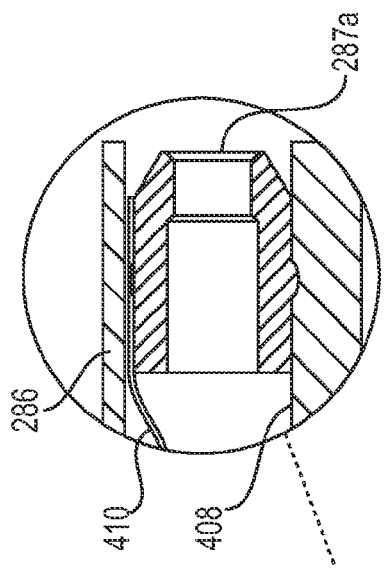
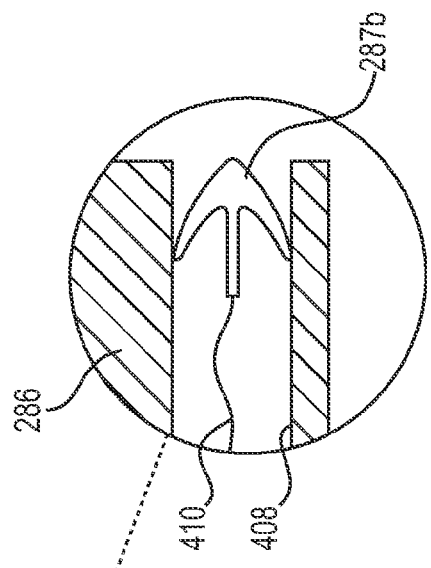
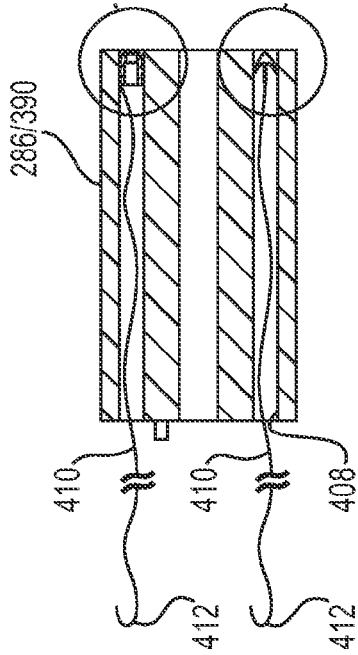
Fig. 21B
Fig. 21C
Fig. 21A

APPARATUS, SYSTEM AND METHOD OF MINIMALLY INVASIVE REPAIR OF PELVIC ORGAN PROLAPSE

BACKGROUND

A patient's pelvic floor includes of a sheet of muscles and ligaments that support the organs that fill the patient's pelvic cavity, namely the bladder, uterus, colon and small intestine. If these supporting tissues stretch or weaken, some of the patient's internal organs may sink lower in their body, or prolapse into the vagina. This condition is referred to as pelvic organ prolapse (POP). There are generally four forms of POP, including: cystocele, which is a weakening of the vaginal wall, allowing the bladder to protrude into the vagina from above; rectocele, which is a weakening of the back wall of the vaginal that allows the rectum to protrude into the vagina; vaginal vault prolapse (uterine prolapse) in which the uterus intrudes into the vagina from above; and enterocele is which the small intestine descends to protrude into the vagina.

Surgery is an option that offers relief from the undesirable effects of POP. In generally, the surgeries include some form of a trans-vaginal or an open abdominal approach or incision, and these approaches might present the patient with several days of rest and recovery.

SUMMARY

A system for repair of a prolapsed organ in a patient includes a support and a deployment instrument having a handle extending from a barrel and a trigger offset from the handle. The trigger is operable to advance the support out of the barrel of the deployment instrument and into the patient.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 12 is a side schematic view of support material configured to support a bladder in the treatment of pelvic organ prolapse.

FIG. 16 provides various embodiments of an expandable pelvic organ prolapse support material in a compacted state and an expanded state.

FIG. 17 provides various embodiments of an expandable support including a urethra channel configured to support a bladder in the treatment of pelvic organ prolapse.

FIG. 21A is a side cross-sectional view of the anchor introducer cartridge illustrated in FIG. 14.

FIGS. 21B and 21C are partial side cross-sectional views of anchors loaded into the anchor introducer cartridge illustrated in FIG. 21A.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Embodiments provide an apparatus, system, and method for the minimally invasive treatment of pelvic organ prolapse. Embodiments provide an apparatus, system, and method for the repair of pelvic organ prolapse through a small incision (less than 2 cm) within a patient in a minimally invasive manner. In one embodiment, access to the patient is gained laproscopically or vaginally or through the urethra via an opening of less than 2 cm, preferably less than 1 cm. Through this opening, the apparatus, system and method provides for the location, measurement, and placement of a support material inside the patient to repair and treat pelvic organ prolapse.

Embodiments provide a method and apparatus for measuring the size and placement location of a support material prior to implanting the support material into the patient. Additional embodiments provide methods and products for first placing support material into a patient and then anchoring the support material to a patient in the treatment of pelvic organ prolapse.

The apparatus, system, and methods described herein allow the minimally invasive access to the internal organs of a patient suffering pelvic organ prolapse for locating and measuring distances to landmarks within the patient, measuring support material based on the measured distances, and the placement and anchoring of support material within the patient.

The treatment of pelvic organ prolapse (POP) includes the treatment of cystocele, rectocele, vaginal vault prolapsed, and enterocele. Many of the embodiments described herein, while suited to treating various forms of POP, are ideally suited to the treatment of cystocele.

Figure 1:
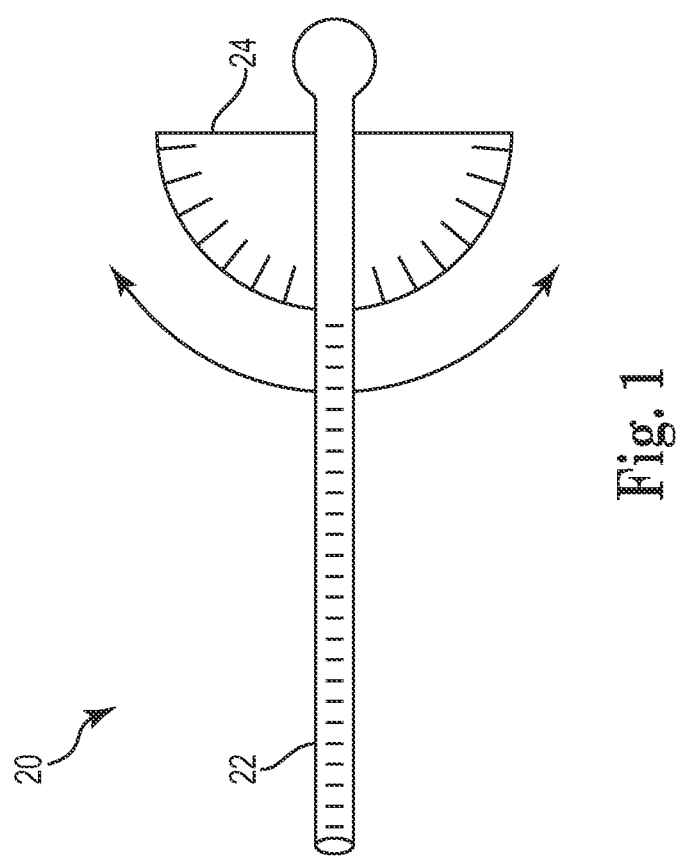
FIG. 1 is a top view of a device for measuring multiple locations within a space for placement of material in the treatment of pelvic organ prolapse.

FIG. 1 is a top view of a device 20 configured to measure a size of support material and identify attachment locations for the placement of the measured support material according to one embodiment. Device 20 includes a scope 22 extending from a protractor 24. In one embodiment, scope 22 as provided as a cystoscope that includes optical viewing and measuring capabilities disclosed within a cannula of scope 22. In one embodiment, scope 22 includes gradient markings on an exterior surface of the cannula to assist in measuring the distance and location of the desired placement of a support material within a patient undergoing pelvic floor repair. In one embodiment, scope 22 moves laterally relative to protractor 24 to assist in determining an angular location of the desired placement of support material within a patient. To this end, scope 22 in combination with protractor 24 provides for the linear measurement of depth in addition to the angular inclination or declination when measuring the patient for placement of the support material. For example, in one embodiment device 20 is employed to collect length and angle measurements within a patient to mathematically determine an appropriate size for support material relative to the pelvic floor of the patient. The lengths and angles measured with device 20 are subsequently transferred to the support material, which is cut or otherwise modified according to the measurements. Thereafter, the appropriately sized support material is placed within the patient and attached to the landmarks measured identified with device 20.

Suitable materials for fabricating device 20 include stainless steel materials appropriately modified to include optical instruments suited to function as a cystoscope.

Device 20 is configured to measure the radius and angle of at least two locations within a patient, and preferably at least four locations of the patient for the placement of support material onto landmarks of the patient. Suitable landmarks include the arcus tendineus, the sacrospinous ligament, the sacrum, and the pubic symphysis to name several. In one embodiment, scope 22 is provided with a deployment mechanism, such as an extensible finger, that is deploy from a distal end of scope 22 to anchor or fix in place the measured/sized support material.

In one embodiment, scope 22 is provided with at least two degrees of freedom relative to protractor 24 and is thus configured to measure and record inside measurements of the patient (for example along the pelvic floor) while maintaining a proximal end of device 20 in a relatively fixed location (for example at an entrance of the vagina).

Figure 2:
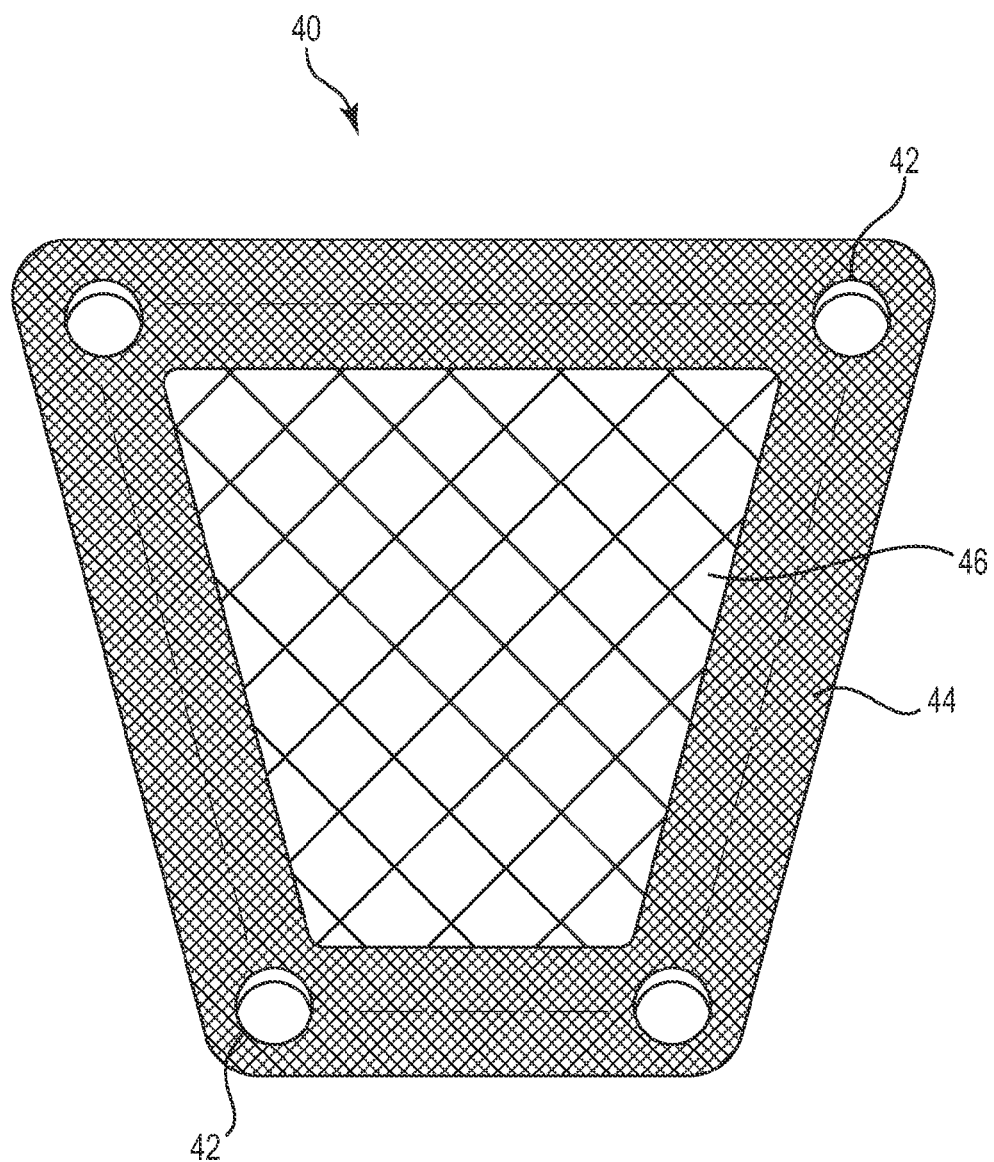
FIG. 2 is a top view of material configured to treat pelvic organ prolapsed, for example in a pelvic floor replacement surgical procedure.

FIG. 2 is a top view of support material 40 according to one embodiment. Support material 40 is provided as a "pre-shaped" support in one embodiment and includes at least one fixation location 42 placed on a reinforced boundary 44 of material 40. In one embodiment, the fixation locations 42 are provided as rivets configured to receive an anchor. In one embodiment, the reinforced boundary 44 is provided as a mesh having a pore size that is smaller than a pore size of the remaining support material 40. For example, in one embodiment a central portion 46 of support material 40 is provided with a pore size of about 1121 microns, and a reinforced boundary of material 40 is provided with a pore size of less than 900 microns. The pore size of the central portion 46 is selected to encourage tissue ingrowth that will ultimately hold the implanted support material in place within a patient. The smaller pore size of the central portion 46 has smaller pores which relate to a tighter weave (higher density) that is configured to support the boundary 44 of material 40.

Suitable materials for fabricating at least the central portion 46 of support material 40 include polypropylene or synthetic materials, cadaver tissue, dermis, fascia lata, or engineered materials.

Figure 3:
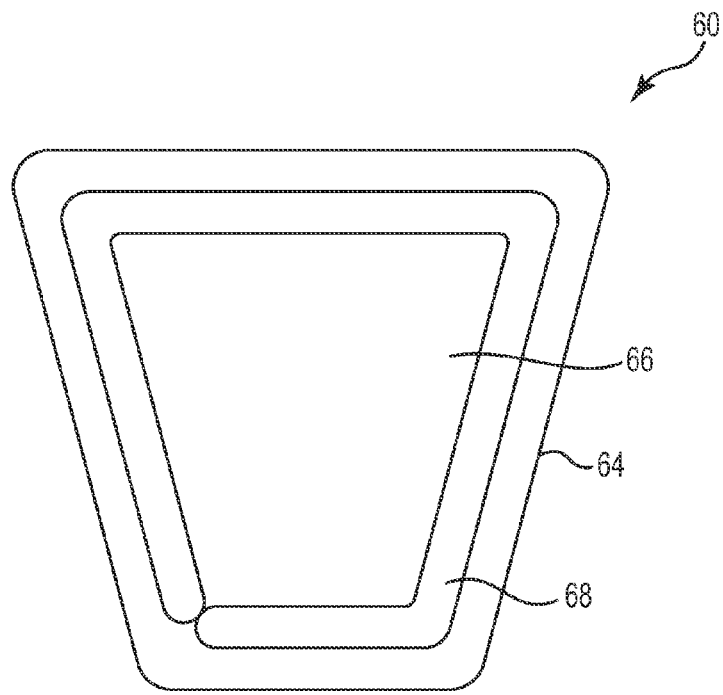
FIG. 3 is a top view of another embodiment of material configured to treat pelvic organ prolapse.

FIG. 3 is a top view of another embodiment of a support material 60. It is desirable to provide support material 60 in a compact form that can be delivered into the patient through minimally invasive techniques and then expanded and employed within the patient to repair or support the pelvic floor. In one embodiment, support material 60 includes a boundary 64 surrounding a central portion 66 and an inflation bladder 68 located on a perimeter of boundary 64. In one embodiment, support material 60 is provided in a deflated and folded format suited for delivery into the patient through a trocar or small incision. After placement of support material 60 as desired by the surgeon, bladder 68 is inflated to expand material 60 and boundary 64. To this end, a relatively large area of support material 60 may be collapsed into a small bundle that is suited for delivery laproscopically, vaginally, or through the urethra and subsequently expanded to a suitably large area for repair and support of the pelvic floor of the patient.

In one embodiment, central portion 66 is provided as mesh material and bladder 68 is provided as inflatable bladder that is attached to the boundary 64.

Figure 4:
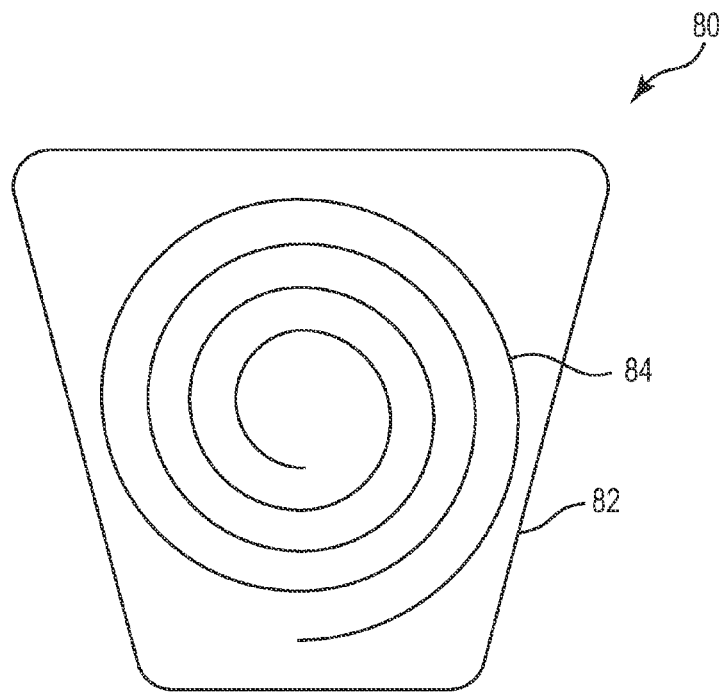
FIG. 4 is a top view of another embodiment of material including a biasing element and configured to treat pelvic organ prolapse.

FIG. 4 is a top view of another embodiment of a support material 80. In one embodiment, support material 80 includes a housing 82 and a biasing mechanism 84 disposed within housing 82. In one embodiment, housing 82 is fabricated from a mesh material and biasing mechanism 84 is provided as a coil spring. Similar to support material 60 described above in FIG. 3, support material 80 is configured to be delivered in a compact size through a minimally invasive access port into the patient after which support material 80 is expanded via mechanism 84 to "full" size suitable for reinforcing and supporting the pelvic floor.

Figure 5:
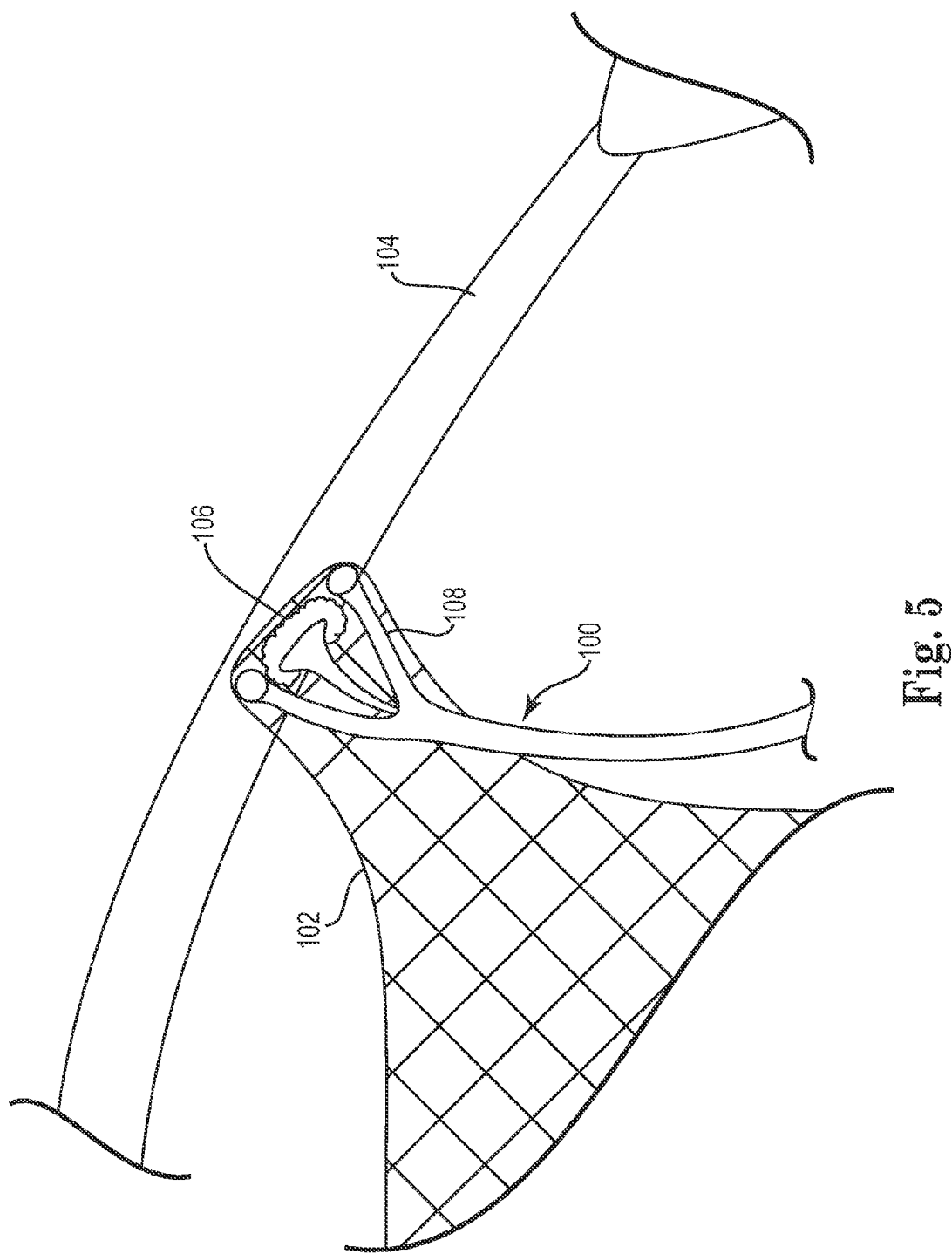
FIG. 5 is a schematic view of a device configured to hold a support material in place and deliver attachment material to fix the support material to a landmark of the body.

FIG. 5 is a perspective schematic view of a device 100 configured to deliver and hold support material 102 in place relative to a landmark 104 and subsequently anchor support material 102 to a landmark 104 with anchor material 106. The landmark 104 includes anatomical sites such as the sacrum, the arcus tendineus, the sacrospinous ligament, the ischial spine, or the pubic symphysis.

In one embodiment, device 100 is sized for delivery through a laproscopic trocar or through a vaginal incision and includes placement members 108. In one embodiment, placement members 108 are movable at least laterally to assist in placement of support material 102 against landmark 104. In another embodiment, placement members 108 are configured to move laterally and axially (in/out) to assist in placement of support material against landmark 104.

Suitable materials for support material 102 include synthetic materials such as polypropylene mesh, biological materials such as human or animal tissue, or genetically modified or other engineered tissues.

In one embodiment, anchor material 106 is provided as an adhesive. Suitable adhesives include a self-assembling adhesive delivered from device 100 and configured to attach support material 102 to landmark 104. In one embodiment, anchor material 106 is provided as a fibrin or a fibrin polymer that self-assembles into a durable matrix upon exposure to an energy source, such as ultraviolet light. In one embodiment, anchor material 106 is provided as adhesive that is moisture-cured such that placement of anchor material 106 within the anatomy of the patient results in anchor material 106 hardening to hold support material 102 against the landmark 104. In one embodiment, anchor material 106 is provided as a biocompatible sealant, and in other embodiments anchor material 106 is suitably provided as one of a bioabsorbable hyaluronic acid material, a chitin material, or a chitosan material.

Figure 6:
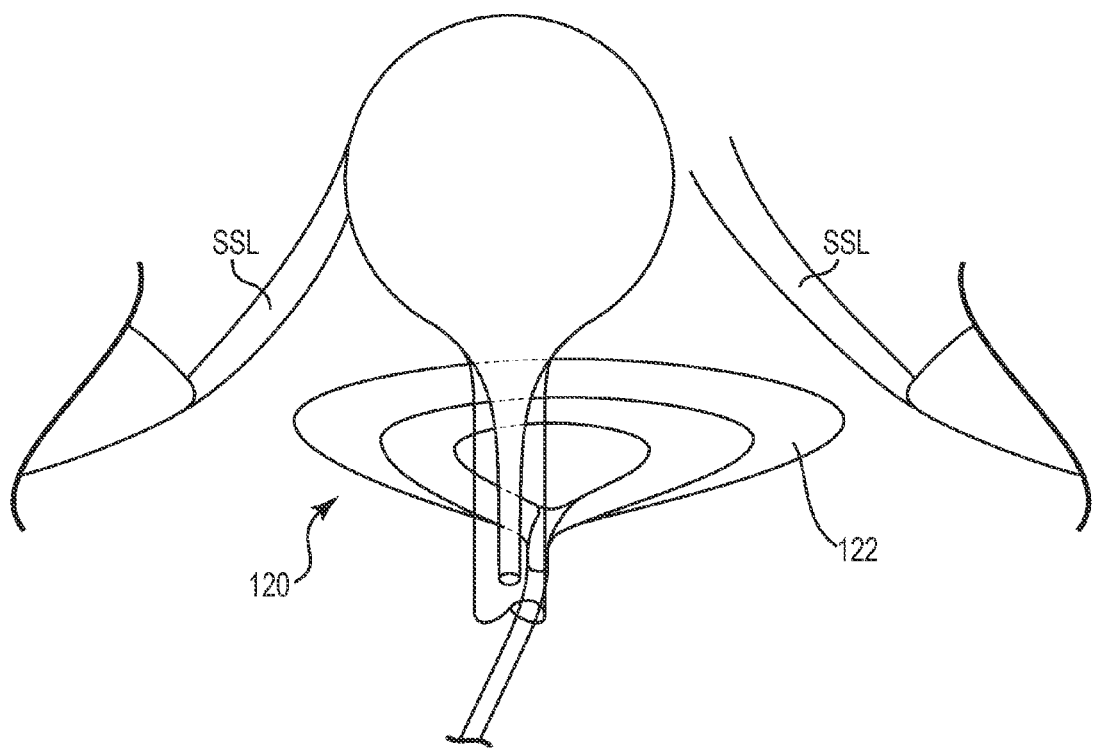
FIG. 6 is a perspective view of a support balloon inserted between the bladder and the vagina in the treatment of pelvic organ prolapse.

FIG. 6 is a perspective schematic view of a device 120 configured to support the bladder. In one embodiment, device 120 includes an inflatable reservoir 122 that is configured to be placed within the vagina, around a portion of the urethra, and under the bladder. The reservoir 122 is expanded, for example by inflation with a fluid, and the reservoir expands to fill the space between the ischial spine and the sacrospinous ligaments. In one embodiment, the volume to fill the reservoir 122 corresponds to, or is calculated to correlate to, a desired size of support material. For example, inflating reservoir 122 with 90 cm$^3$ of liquid expands device 120 to a size that correlates to the amount of liquid injected into the reservoir 122 (90 cm$^3$). Thereafter, the surgeon refers to a chart that correlates the amount of liquid injected into the reservoir with a size of support material. When the support material is cut to the desired size, it appropriately and closely fills the space between the landmarks, for example between the ischial spine and the sacrospinous ligaments.

In one embodiment, device 120 is in a system including the above-referenced chart, where the chart correlates the volume employed to inflate reservoir 122 to a size and shape of support material. Embodiments of the chart include columns and rows of data printed on one side, and in one embodiment such a chart is provided as a template that may be followed to suitably craft/cut-to-size the support material to the appropriate size and shape specified by device 120.

Figure 7:
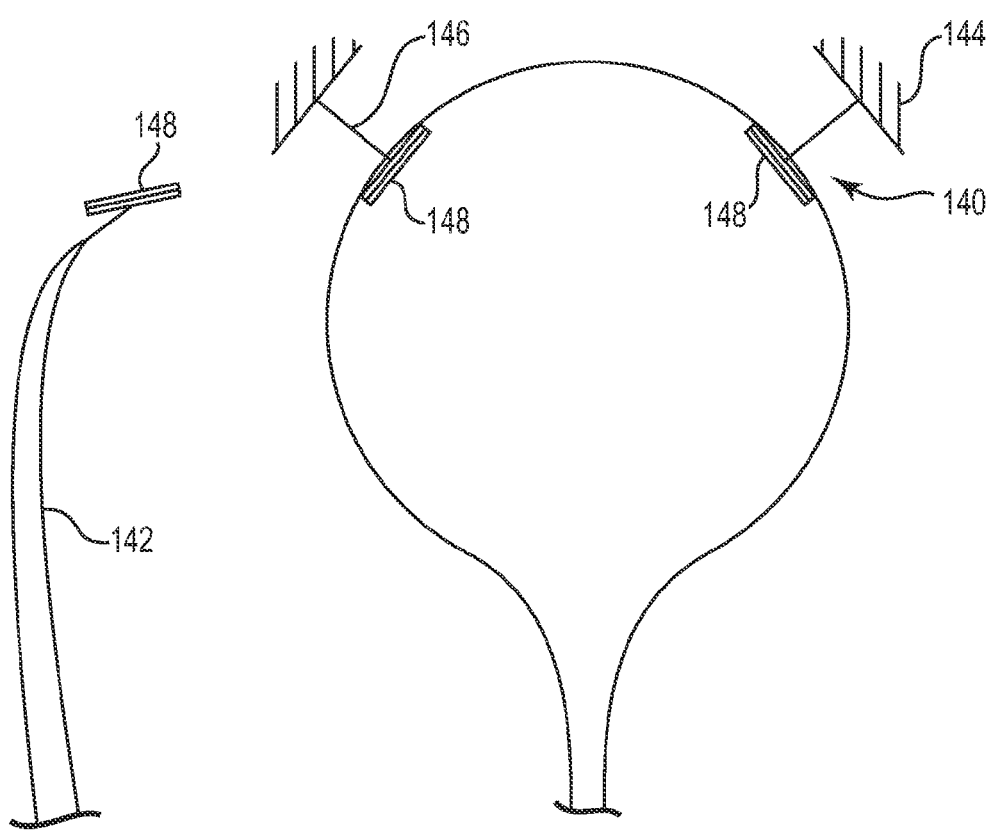
FIG. 7 is a schematic view of anchor is deployed to support the bladder in the treatment of pelvic organ prolapse.

FIG. 7 is a perspective schematic view of a device 140 employed to elevate the bladder and relieve the effects of pelvic organ prolapse. In one embodiment, device 140 is provided as one or more anchors that are delivered via a surgical instrument 142 to the bladder. The anchors generally penetrate a portion of the patient's tissue and include fixed anchors and anchors that "adjust" by movement relative to a suture passing through the anchor. The devices 140 may be suitably deployed by access through the urethra to the bladder or through the abdomen (e.g., via a trocar) to the bladder.

In one embodiment, device 140 is inserted from a location exterior the bladder to a location inside the bladder, were device 140 includes a deployed anchor that supports the bladder against the downward force of gravity. In one embodiment, device 140 is introduced through the urethra to a wall of the bladder and anchored to support 144, which includes tissue or a pre-placed support 144. Embodiments of surgical instrument 142 are configured and sized for delivery through a laparoscopic trocar, a vaginal incision, or through the urethra into the bladder. With this in mind, in one embodiment surgical instrument 142 is inserted within the urethra into the bladder to enable instrument 142 to deliver device 140 through a wall of the bladder into supporting tissue 144.

In one embodiment, device 140 includes a suture line 146 and an anchor 148. Suture line 146 is configured to tension device 140 between supporting tissue 144 and the bladder and can be provided as an adjustable suture line 146. The anchor 148 is movable relative to line 146 and is configured to align with the suture line 146 to enable penetration of device 140 through tissue. After delivery of device 140, the anchor 148 swivels to a position "broadside-on" that is not aligned with suture line 146 and is thus positioned to hold the anchor 148 in its deployed position.

Figure 8:
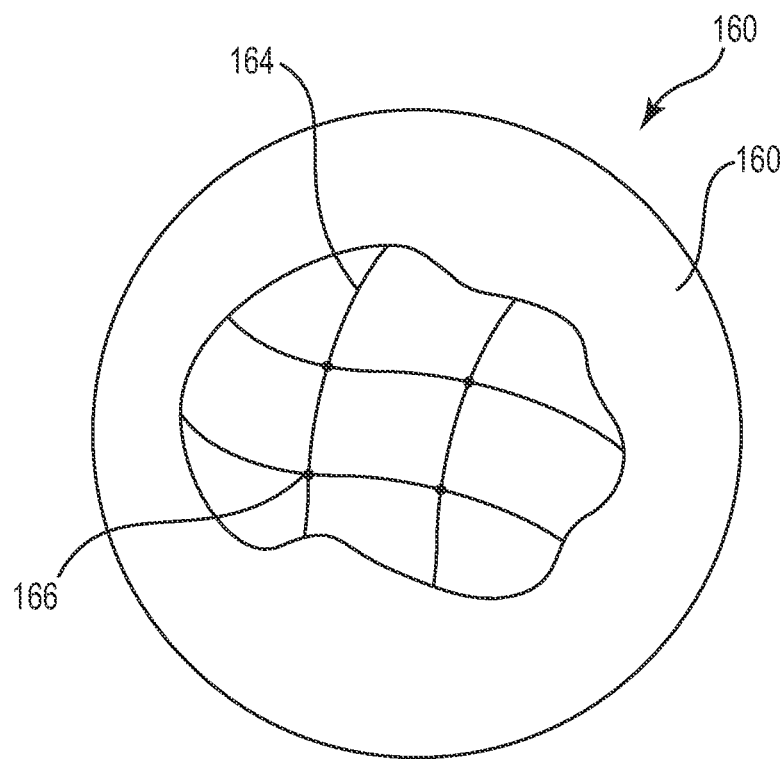
FIG. 8 is a top view of a support material including anchors located at nodes according to one embodiment.

FIG. 8 is a top view of another embodiment of a support material 160 that is configured to be implanted in a minimally invasive manner in an initial compact form that subsequently expands to a larger final/deployed size/format. In one embodiment, support material 160 includes a boundary 162 supporting a mesh 164 that provides a grid of intersecting support lines that intersect at nodes 166. In one embodiment, body 162 is flexible, supports the mesh 164, and is configured to be attached to anatomical features of the patient. The nodes 166 are employed to anchor the device 160 to portions of the pelvic floor or to anatomical features such as the bladder.

Figure 9A:
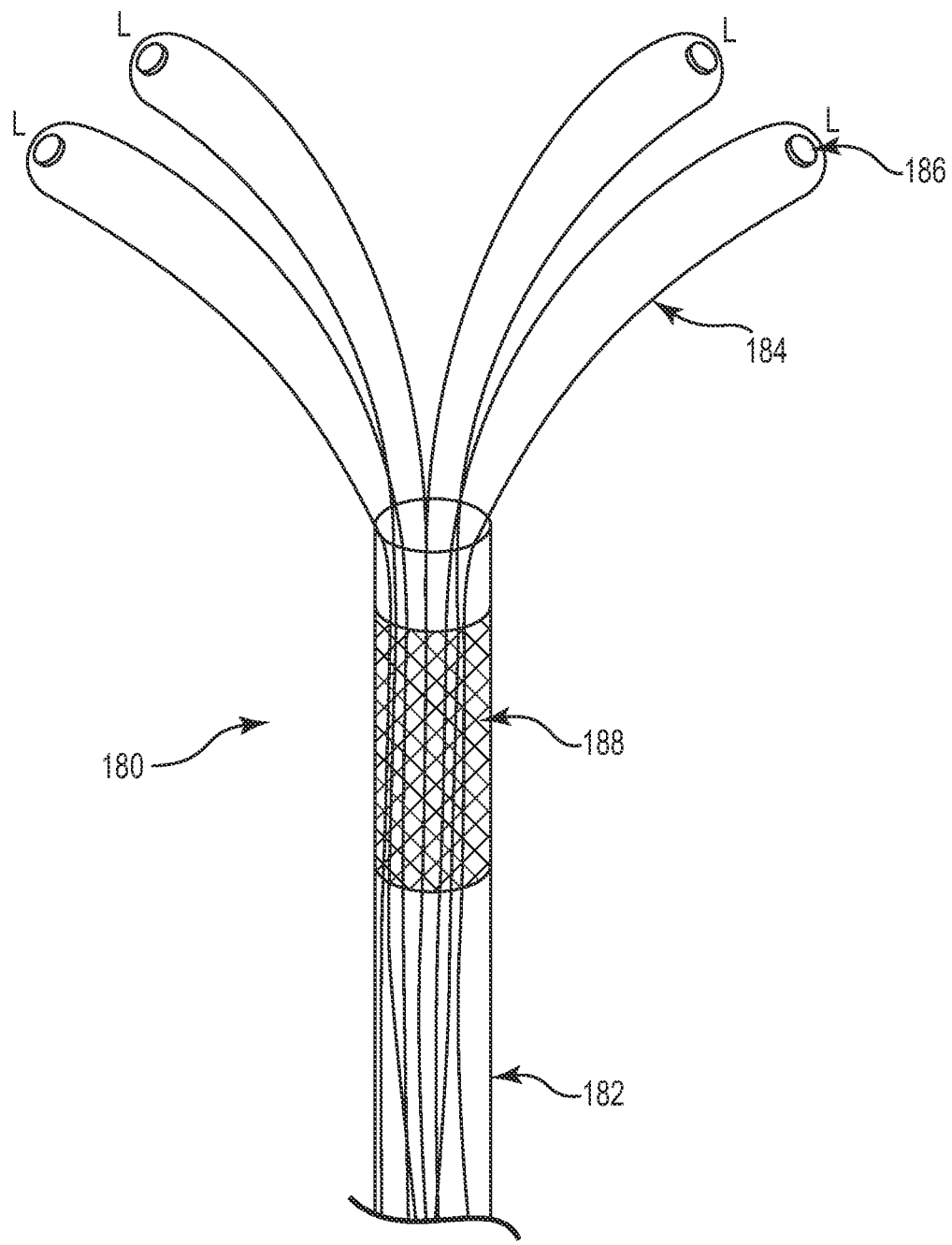
FIG. 9A is a perspective view of a device including a cannula maintaining folded support material and including anchors attached sutures that may be usefully employed to deploy the support material.

FIG. 9A is a perspective view of another embodiment of a device 180 for the minimally invasive delivery of support material to treat a patient for pelvic organ prolapse. In one embodiment, device 180 includes a cannula 182, and extensible members 184 that are movable out of the cannula 182 to deliver anchors 186 to a selected site and ultimately to deliver a support material 188 to the site using. In one embodiment, cannula 182 is provided as a stainless steel tube sized to be inserted into the patient through a "small" incision of smaller than 2 cm. In one embodiment, cannula 182 includes optical components and is configured as a cystoscope. In one embodiment, extensible members 184 are provided as metal fingers that deliver sutures 184 and anchors 186 to a landmark L site within the patient. In one embodiment, extensible members 184 are sutures with pre-attached anchors 186. The support material 188 can be folded to be advantageously stored within cannula 182 until a distal end of cannula 182 is delivered near the landmark L site, at which point the anchors 186 are attached to the landmark L and the cannula 182 is removed leaving sutures 184 connected to anchors 186.

Figure 9B:
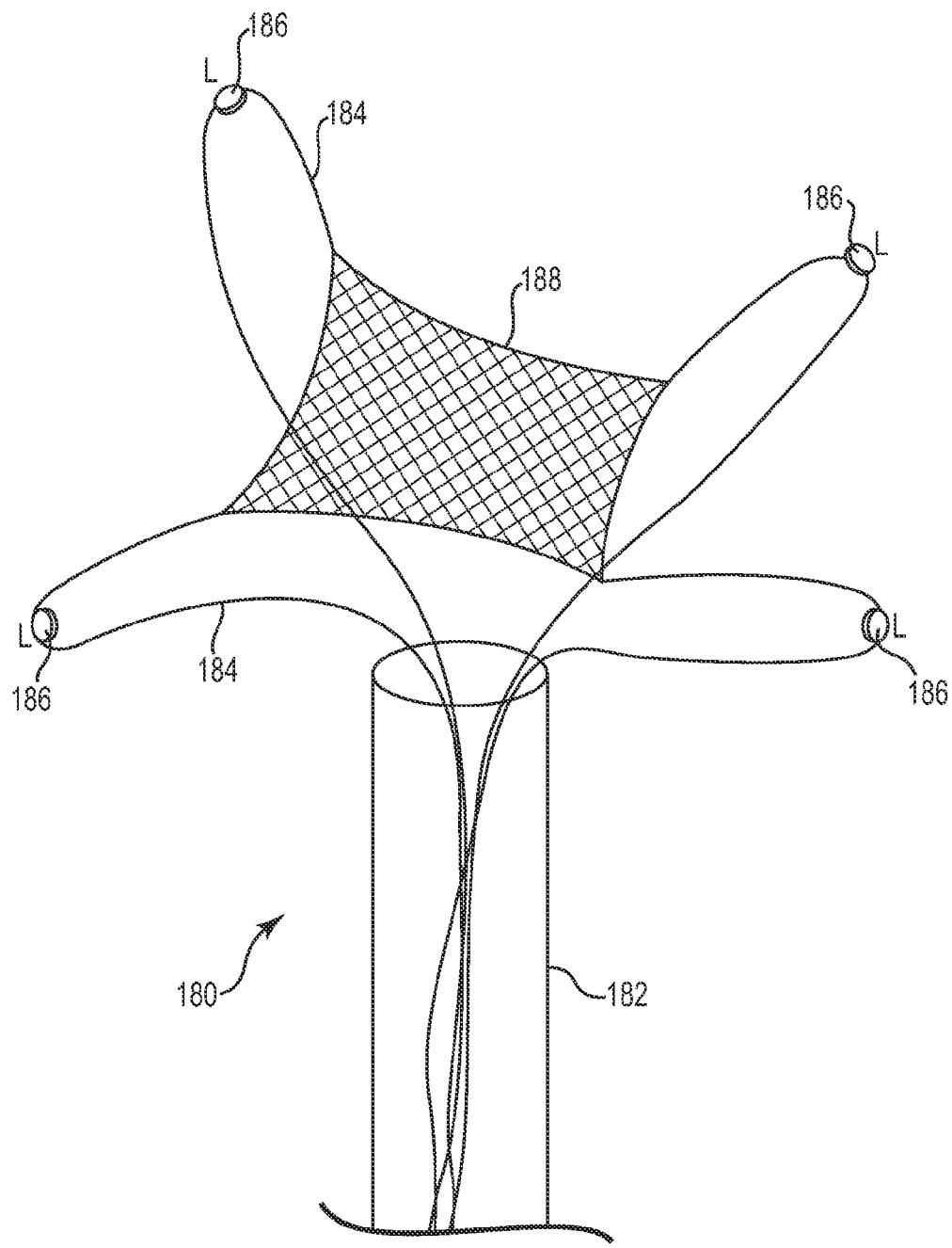
FIG. 9B is a perspective view of the device illustrated in FIG. 9A including the support material deployed out from the cannula.

FIG. 9B is a perspective view of cannula 182 partly removed from the surgical site and leaving support material 188 attached to the landmarks L via the sutures 184 and anchors 186. After removal of cannula 182, sutures 184 are employed to pull support material 188 toward the landmarks L. For example, in one embodiment sutures 184 function as a pulley to deliver support material 188 upward into position relative to the landmarks L (e.g., sacrospinous ligament or arcus tendineus). In this manner, the folded and compact support material 188 is stowed in cannula 182 and suited for delivery to the landmark L site in a minimally invasive form, after which the support material 188 is deployed from cannula 182, expanded, and attached to the landmark L site with the sutures 184 and anchors 186.

Figure 10:
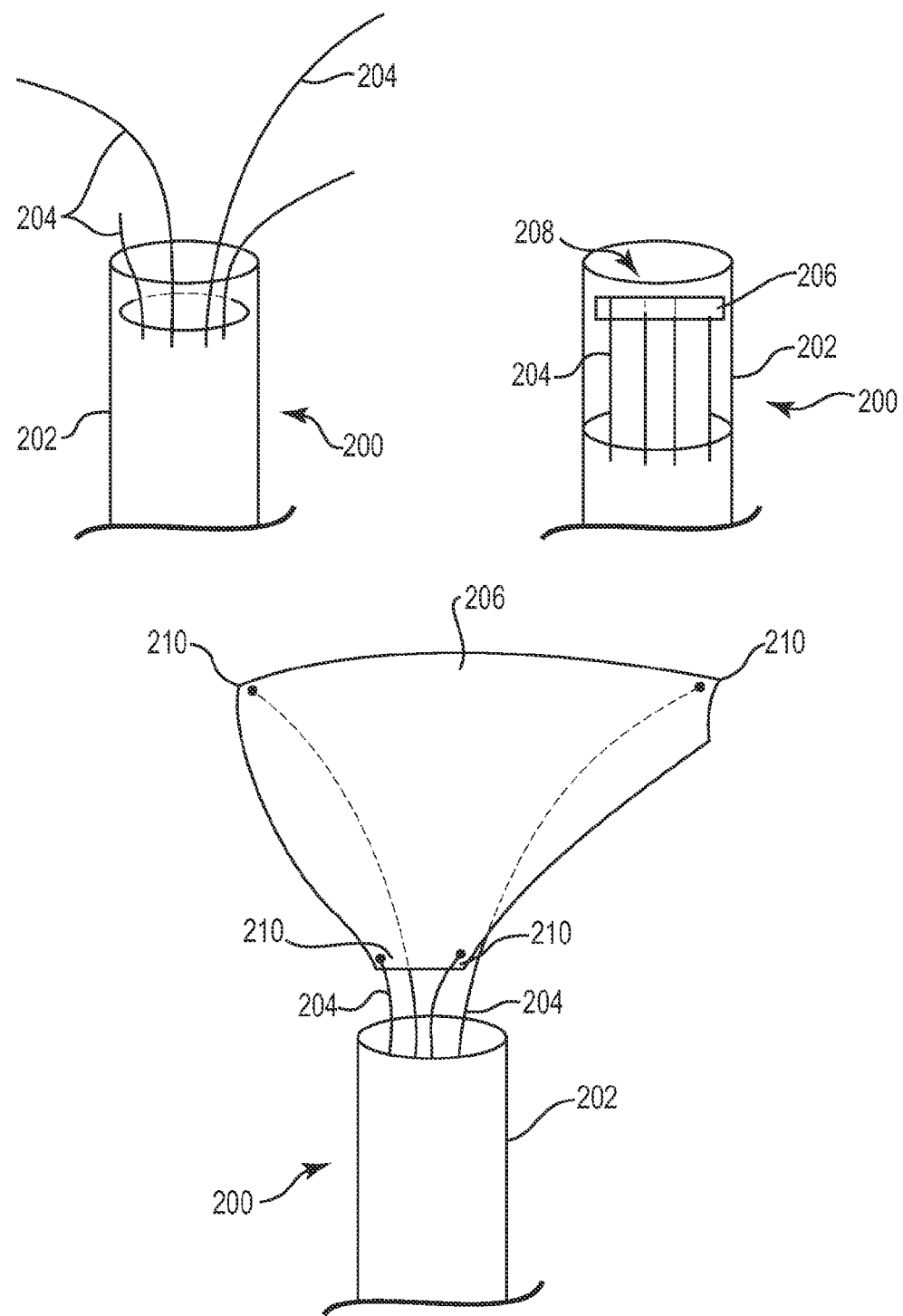
FIG. 10 is a perspective view of a device including a cannula maintaining extensible fingers that are configured to measure distances to a landmark, transfer the measured distances to a support material for custom sizing, and deliver the custom-sized support material to the landmark according to one embodiment.

FIG. 10 provides various embodiments in perspective view of a device 200 configured to locate landmark sites for attachment of support material, measure a distance between the respective landmark sites, transfer the measured distances to the support material for custom sizing, and then deliver the custom-sized support material to the landmark.

In one embodiment, device 200 includes a delivery introducer 202 maintaining multiple extensible fingers 204. One embodiment of the delivery introducer 202 is provided as a cannula having optical components in the form of a cystoscope. In one embodiment, extensible fingers 204 extend from a distal end of introducer 202 to locate multiple independent landmark sites. The location of the multiple independent landmark sites is recorded by introducer 202, for example digitally or an analog form as a distance that each individual finger 204 is extended out of and away from introducer 202. The location data is employed to cut or otherwise custom-size support material that will fit the individual patient as measured by device 200. The support material 206 is customized and attached to the extensible fingers 204 and retracted into the introducer 202 as illustrated at 208 for delivery into the patient. In this configuration, the introducer 202 and support material 206 are configured to be delivered in a minimally invasive matter to the patient near or adjacent to the landmark sites. Thereafter, the extensible fingers 204 are extended from a distal end of the introducer 202 and delivered to the landmark sites for attachment of respective corners 210 of support material 206 to the landmark sites.

In one embodiment, fingers 204 configured to take on a set or otherwise have memory. Suitable such "memory" fingers 204 are fabricated from memory material such as NiTiNOL (a nickel-titanium alloy developed by the Naval Ordinance Laboratory).

In one embodiment, one of the four corners 210 is attached to each of the sacrum, pubic symphysis, and to locations along the ischial spine, for example along the arcus tendineus ligament and the sacrospinous ligament. The extensible fingers 204 are configured to locate these landmarks, measure a distance to these landmarks, and translate that measured distance to support material 206. The support material 206 is custom sized based upon these measurements, for example by the surgeon who uses a scissors to cut the support material 206 to the desired calculated shape. Thereafter, the support material 206 is loaded in cannula 202 for subsequent delivery to the landmarks.

Figure 11:
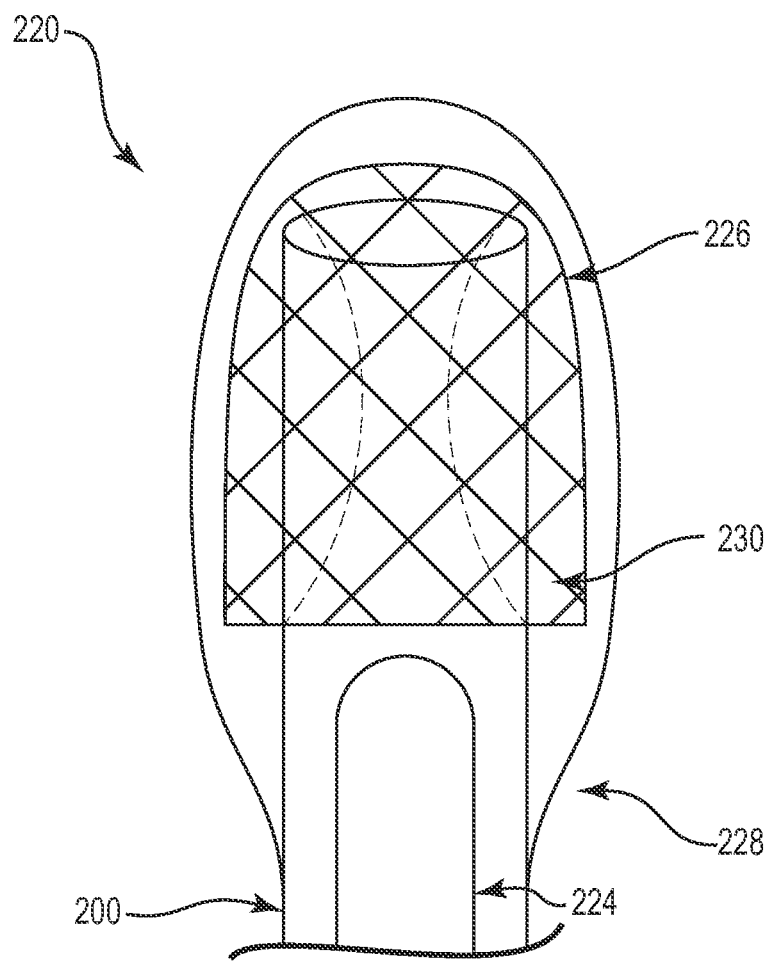
FIG. 11 is a side view of another embodiment of a device including support material communicating with a push rod and including a dissolvable housing securing the support material over the push rod.

FIG. 11 is a side schematic view of another device 220 configured to deliver support material to a patient to support the pelvic floor or other organs via a minimally invasive surgical procedure. In one embodiment, device 220 includes a cannula 222, a push rod 224 disposed within cannula 222, and support material 226 carried by the cannula 222 and protectively covered by a dissolvable film 228. In one embodiment, rod 224 is configured to move axially within cannula 222 to deliver support material 226 to an identified location within the patient. In the delivery configuration, dissolvable film 228 effectively covers support material 226 until introduced within the body. In one embodiment, the temperature of the body or the moisture within the body, or both, contributes to dissolving the film 228, which prepares (or frees) the support material 226 to be released. Suitable film material for film 228 includes polyvinyl acetate films that are dissolvable in aqueous solutions. Thereafter, push rod 224 moves out of the distal end of cannula 222 to deliver the support material 226 into the patient. In one embodiment, cam arm(s) 230 are provided that move out as the push rod 224 most axially, and the outward motion of the cam arm(s) 230 directs the support material 226 to the pre-selected landmarks.

FIG. 12 is a side schematic view of a device 240 configured to elevate and support the bladder with the understanding that the bladder is presented in an inverted form to better illustrate the extension of sutures 248.

In one embodiment, device 240 includes a support 242 that is attached to the bladder by a disc 244 where the support 242 is secured to a landmark of the patient by an attachment mechanism 246. In one embodiment, the attachment mechanism 246 includes a suture line 248 attached to support 242 on one end and secured to anchor 250 on an opposite end.

In one embodiment, support 242 and disc 244 are introduced or placed through the urethra, for example by a thin-walled cannula introducer that traverses the urethra to the bladder, a minimally invasive implantation approach that does away with incisions into the patient's tissue. In one embodiment, support 242 and disc 244 are laproscopically delivered in a suprapubic approach.

In one embodiment, support 242 is provided as an open mesh configured to encourage tissue ingrowth and includes radially spaced circular bands interconnected by strands that radiate from a central portion of support 242.

Figure 13:
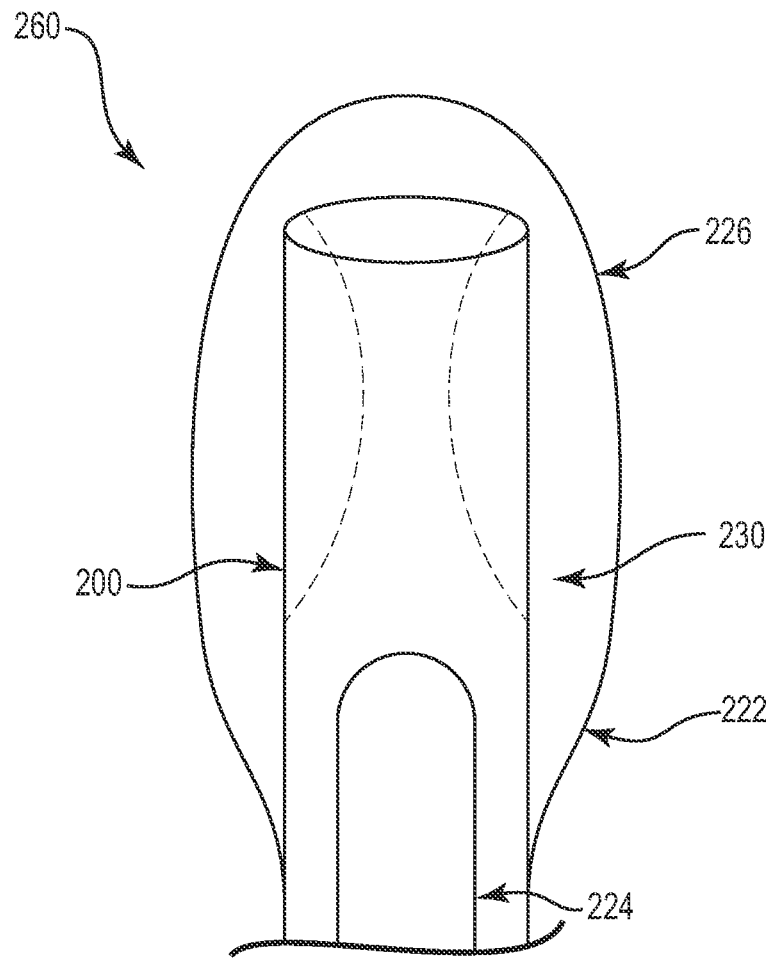
FIG. 13 is a side schematic view of another embodiment of a device for the treatment of pelvic organ prolapse including a tube and an arm disposed in the tube that includes a cauterization tool.

FIG. 13 is a side schematic view of the device 260 configured to deliver a support to the patient in a minimally invasive manner related to treatment of all the court in prolapse. In one embodiment, device 260 is similar to device 220 (FIG. 11) described above and includes an introducer cannula 222 maintaining a push rod 224 that most axially along cannula 222 to deliver mesh 226 to a landmark within the patient. In one embodiment, cam arm(s) 230 are provided that move out as push rod 224 moves up, and in so doing functions to displace mesh 226 radially and laterally to the identified landmarks. In one embodiment, device 260 includes a cautery 262 that communicates with cam anus 230, where cautery 262 is configured to energetically attach mesh 226 to the identified landmark. In one embodiment, cautery 262 is provided as an electro-cautery wand. In one embodiment, cautery 262 is provided as an ultrasonic welder or other high-energy device configured to focus energy between mesh 226 and the identified landmark and fuse the two components together.

Figure 14:
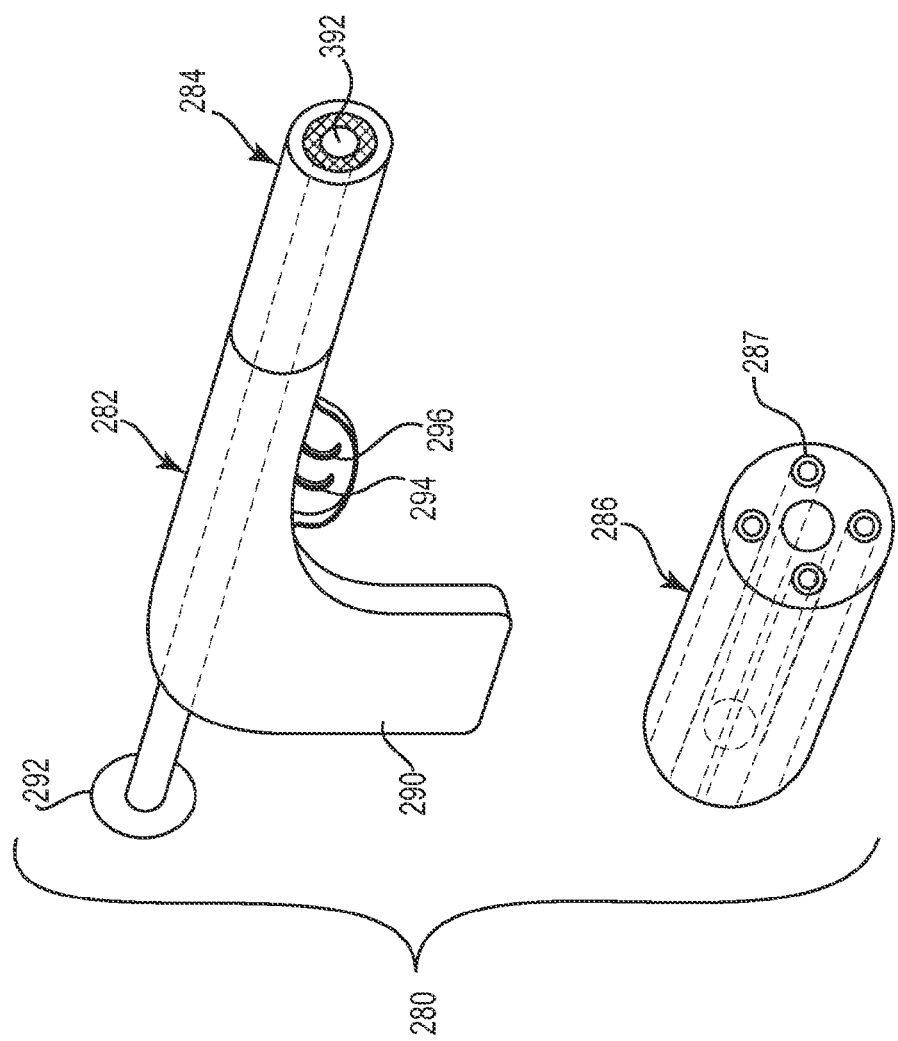
FIG. 14 is a perspective view of another embodiment of a delivery device for placing support material in a minimally invasive manner within a patient to treat pelvic organ prolapse.

FIG. 14 is a perspective view of a mesh delivery system 280 according to one embodiment. In one embodiment, mesh delivery system 280 includes a delivery device 282, a mesh introducer 284 that is removably attachable to delivery device 282 and is configured to introduce mesh into the patient, and a separate anchor introducer 286 that is also removably attachable to deliver device 282 and configured to place anchor attachment devices into the identified landmarks of the patient. An optic scope 292 is provided to allow a surgeon to visualize delivery of mesh and anchors through delivery device 282. In one embodiment, optic scope 292 is a cystoscope or other scope that is axially aligned with a delivery bore of device 282 located on a central longitudinal axis of device 282. Scope 292 is thus suited for viewing inside the patient's body through a trocar, or a small incision, or the urethra.

In one embodiment, mesh introducer 284 is provided as a reloadable cylinder configured to retain mesh or other support material and suitable for delivering the mesh or support material in a minimally invasive manner into the patient. In one embodiment, mesh introducer 284 retains multiple similarly sized meshes, for example multiple trapezoidal meshes having an area of about 52 cm$^2$ each. In one embodiment, mesh introducer 284 retains multiple differently sized meshes, for example multiple meshes each possibly having different areas ranging from about 20 cm$^2$ to about 100 cm$^2$ (i.e., as provided by a "Mattox" style of mesh support template).

In one embodiment, anchor introducer 286 is provided as a cylinder including at least two channels 287, were each channel 287 maintains an anchor. Anchor introducer 286 is removably attachable to a distal end of delivery device 282 and is configured to align a first channel 287 with the axis of the optic scope 292 for the accurate delivery of a first anchor, and configured to rotate to a second channel 287 that is aligned with the optic scope 292 to deliver a second anchor accurate to a second location that is visible through the optic scope 292. In this manner, anchor introducer 286 moves in a revolving fashion to index each channel 287 with the delivery bore of the delivery device 282.

In one embodiment, delivery device 282 includes a handle 290 supporting the optic scope 292 and including a mesh advancer 294 and anchor advancer 296. Mesh advancer 294 is provided as a trigger, the activation of which discharges or delivers the mesh out of a distal end of the mesh introduced 284. Anchor advancer 296 is likewise provided as a trigger, the activation of which discharges or delivers an anchor from one of the channels 287 when anchor introducer 286 is attached to a distal end of delivery device 282.

In one embodiment, device 280 is provided to the operating room in a loaded configuration including mesh loaded into mesh introducer 284 and anchors loaded into anchor introducer 286. For example, a specifically sized mesh may be appropriate for a particular surgical intervention, and this identifying information is placed on an exterior of mesh introducer 284 to allow a surgeon's assistant to choose the size and shape of mesh already pre-loaded into mesh introducer 284. In this manner, a number of mesh introducers 284 may be provided in a clean or even sterile configuration, the appropriate one of which is selected by the surgical staff prior to surgery. In a similar manner, each anchor introducer 286 may be identified by the size and shape of anchor, or the number of anchors, and thus easily identified by the surgical staff prior to surgery. In any regard, device 280 provides a delivery mechanism to deliver a mesh form the mesh introducer 284 that is attached to landmarks by anchors that are placed by the anchor introducer 286.

Figure 15:
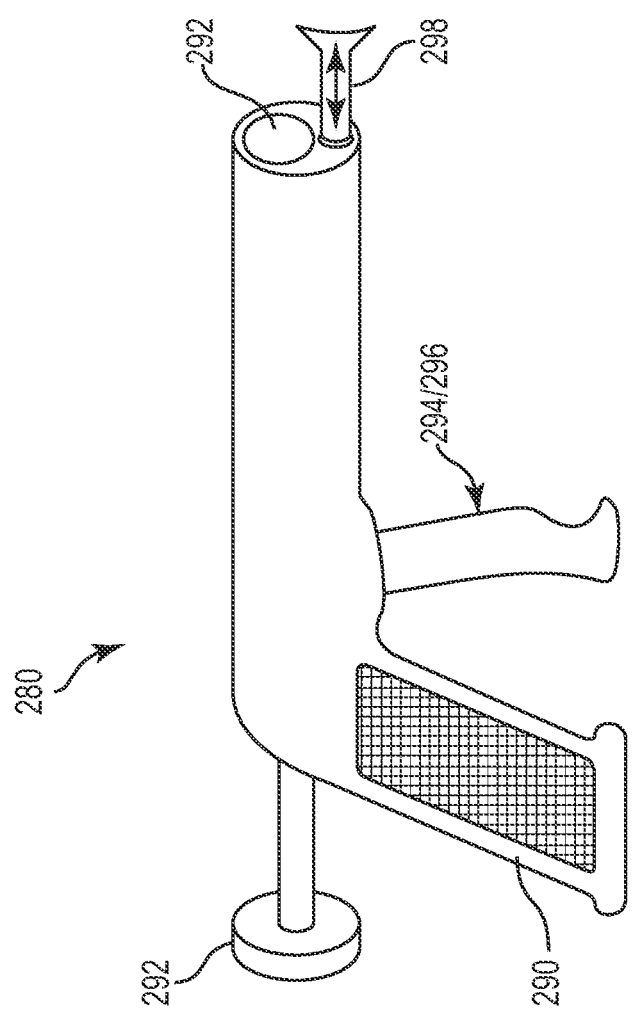
FIG. 15 is a perspective view of another embodiment of a delivery device configured to place support material into a patient in a minimally invasive manner to treat pelvic organ prolapse.

FIG. 15 provides a perspective view of another embodiment of device 280. In one embodiment, device 280 includes optic scope 292 aligned along an optical bore and a delivery introducer 298 provided off of the axis of scope 292 that is configured to deliver anchors and mesh to a landmark. In one embodiment, delivery introducer 298 delivers an anchor attached to a suture to an anatomical landmark such as a sacrospinous ligament. The suture remains attached to the anchor and provides a guideline along which mesh may be delivered to the anchor.

FIG. 16 provides various embodiments of support material 300 each of which is configured to be compacted into a small delivery shape and subsequently expanded to a larger, deployed shape.

In one embodiment, support material 300 is provided as a mesh 302 having a top surface 304 and a lower surface 306 with an inflatable balloon 308 attached to one of the surfaces 304, 306. When balloon 308 is deflated, mesh 302 is configured to roll upon itself into a compact form for delivery into the patient in a minimally invasive manner. When balloon 308 is inflated, mesh 302 expands to its full size suited for deployment or attachment to areas of the pelvic floor of the patient. In one embodiment, balloon 308 is attached to a majority of mesh 302, where mesh 302 includes legs 310 that extend beyond a boundary of balloon 308. Legs 310 are configured to provide attachment locations for support material 300.

FIG. 17 provides various views of a support device 320 configured for minimally invasive delivery to a patient in the treatment of pelvic organ prolapse. In one embodiment, support device 320 includes support material 322 including anchor points 324 and a bladder 326 attached to support material 322, where support device 320 provides a channel 328 configured to receive the urethra of the patient.

Support device 320 is configured to be compacted into a delivery configuration, for example in a roll or folded form for delivery into the patient via an introducer or an insertion tube. Prior to delivery of support device 320, the surgeon would determine a desirable location for the placement of anchors and place the anchors with a suitable device, similar to those described above. Thereafter, support device 320 would be delivered into the patient and attached to the anchors at anchor points 324. In this delivered configuration, the anchor points 324 would be suitably attached to landmarks such as the sacrum, the arcus tendineus, the sacrospinous ligament, or the ischial spine as determined by the surgeon. After attachment, bladder 326 would be inflated to a suitable pressure as determined by the surgeon that would provide an appropriate level of support and/or elevation to the bladder.

Figure 18:
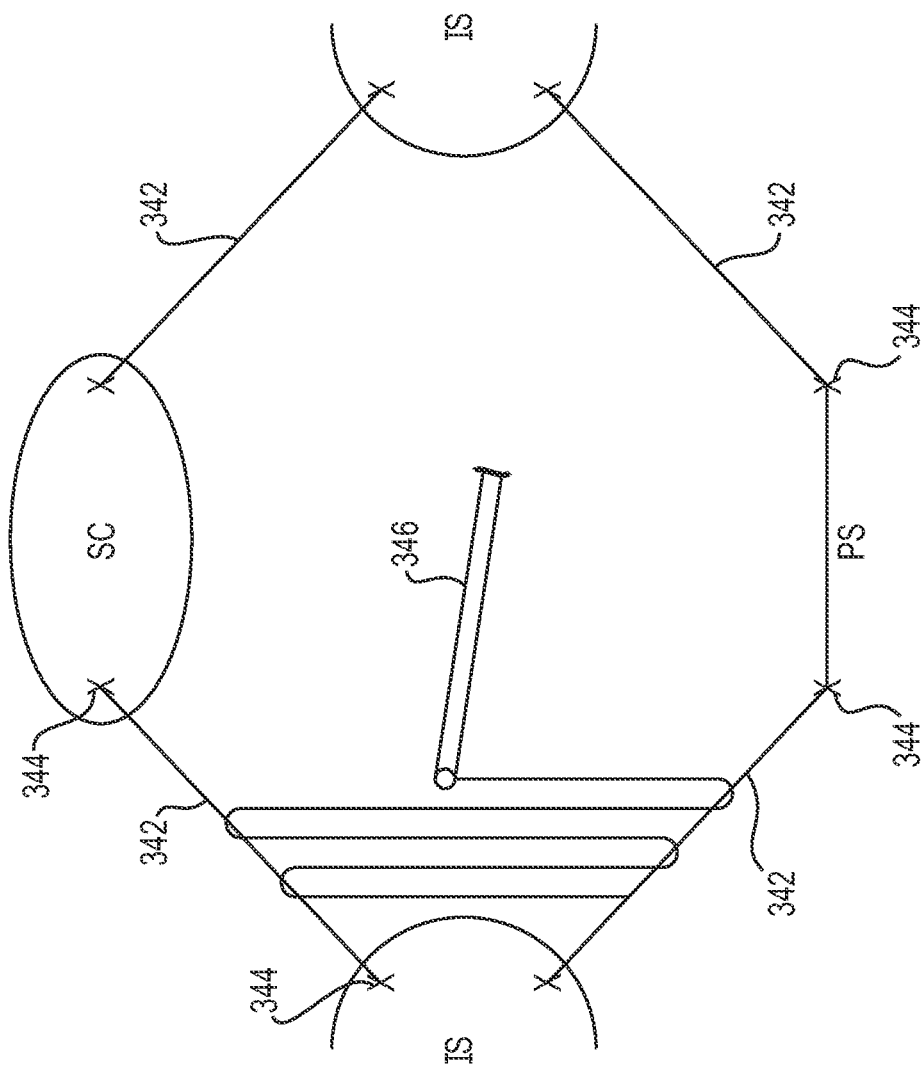
FIG. 18 is a top view of support strands attached between landmarks in a patient and including subsequent strands attached to the support strands to provide an in situ pelvic floor support according to one embodiment.

FIG. 18 is a top schematic view of a portion of a support device 340 according to one embodiment. Support device is configured to be "assembled" inside of the patient to ensure accurate sizing of a support between landmarks of interest to the surgeon.

In one embodiment, support device 340 includes one or more guidelines 342 attached between anchors 344. In one example, a first guideline 342 is secured between the ischial spine (IS) and the sacrum (SC) by anchors 344 and a second guideline 342 is secured between the ischial spine and the pubic symphysis (PS) by other anchors 344. In a similar manner, guidelines 342 are also attached between the pubic symphysis and the ischial spine and between the ischial spine in the sacrum to form a boundary of guidelines 342.

In one embodiment, a delivery device 346 is provided that is configured to spin, spray, or otherwise deliver fibers that extend between adjacent ones of the guidelines 342. For example, in one embodiment delivery device 346 is provided as an electro-spinner that deposits collagen or other suitable biological of synthetic material into the patient through a minimally invasive access port. In other exemplary embodiments, delivery device 346 is configured to deposit a polymer or pre-formed strands of polymer between the guidelines 342. The polymer delivered from delivery device 346 includes thermoplastic polymers and polymers that are configured to cure in the presence of moisture or other energy sources such as light.

Support device 340 is configured to allow a surgeon to place support material at any desired location inside the patient without having to measure a distance between landmark locations and then cut a mesh that corresponds to measured distances. In this sense, support device provides a patient-by-patient custom sized support that is suited to be delivered laproscopically, vaginally, through a perineal incision in a male patient, or through the urethra into the patient.

Figure 19:
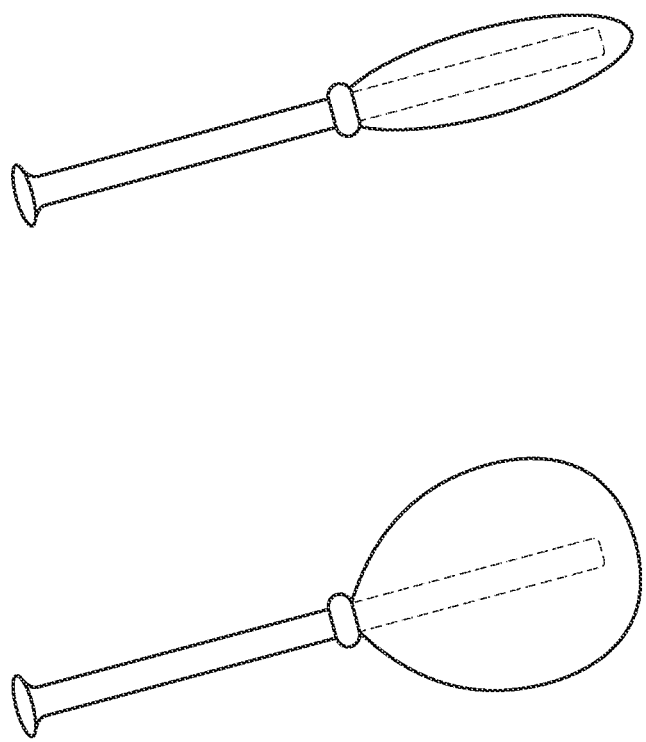
FIG. 19 is a schematic view of a cannula including a balloon configured for dissecting tissue along tissue planes.

FIG. 19 is a schematic view of a cannula including a balloon configured for dissecting tissue along tissue planes. In one embodiment, an inflation fluid is injected into a proximal end of the cannula to inflate a balloon out of a distal end of the cannula. The inflation is selectively controlled by the user to selectively dissect tissue between planes, or to selectively dissect tissue off of a tissue plane.

In another embodiment, a pressurized jet of water is employed to dissect tissue to allow for pelvic floor access and repair. In one embodiment, the water is injected into a cannula and exits from a small diameter needle, where the cannula/needle is inserted transvaginally, endoscopically, or laproscopically to selectively dissect soft tissue planes of the patient undergoing pelvic floor repair.

Examples

Figure 20:
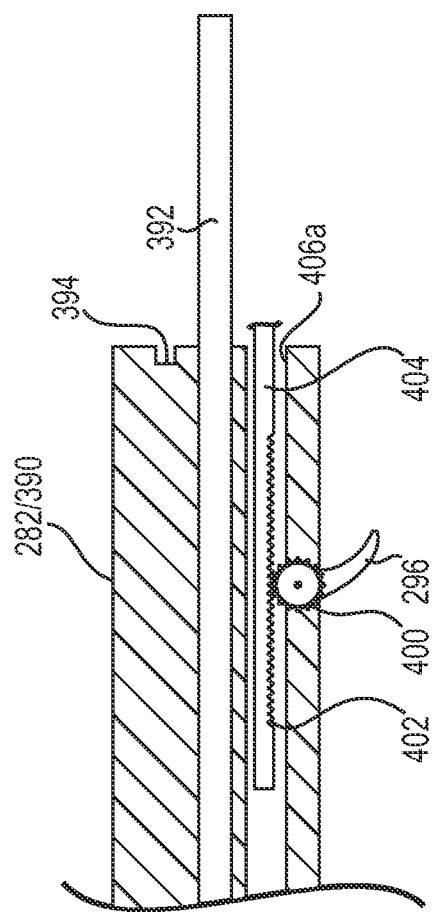
FIG. 20 is a partial side cross-sectional view of the delivery device illustrated in FIG. 14.

Reference is made to FIG. 2, a top view of the support material 40, the delivery device 282 illustrated in FIGS. 14-15 and FIG. 20, and the anchor introducer cartridge 286 illustrated in FIGS. 21A-21C.

The delivery device 282 is employed by the surgical staff to deliver one or more anchors 287 from the anchor cartridge 286 to a landmark within the patient, attach the anchor(s) 287 to tissue at the landmark of the patient, and deliver the support material 40 from the mesh introducer 284 along a suture line to the anchor(s) 287 placed at the landmark.

The mesh introducer 284 or the anchor cartridge 286 are each attachable to combine with the delivery device 282 to define a barrel 390. In one embodiment, the delivery device 282 provides a longitudinally extending pin 392 and each of the mesh introducer 284 and the anchor cartridge 286 engage with and revolve about the pin 392. In one embodiment, the barrel 390 of the delivery device 282 includes a recessed locking latch 394 to which each of the mesh introducer 284 and the anchor cartridge 286 are removably attachable.

The trigger 296 is operable to sequentially advance one of the anchors 287 out of the barrel 390 of the deployment device 282 into the patient each time the trigger 296 is squeezed. Each squeeze of the trigger 296 rotates and indexes a next one of the anchor bores for subsequent deployment. The trigger 294 is operable to advance the support material 40 out of the barrel 390 of the deployment device 282 to the anchor 287 placed in the patient after swapping the anchor cartridge 286 out and replacing it with the mesh cartridge 286.

FIG. 20 illustrates one embodiment of the delivery device 282. In one embodiment, the anchor advancer 296 includes gears 400 that are configured to mesh with gears 402 provided on an advancer rail 404. Squeezing the anchor advancer 296 in a distal direction rotates the gears 400 clockwise, and the gears 400 engage with gears 402 to advance the advancer rail 404 in a proximal direction to eject one of the anchors 287 from the anchor introducer cartridge 286. In this manner, the barrel 390 defines a bore 406 that retains the anchor 287 in operable engagement with the trigger 296 (and the 406 retains the support 40 in operable engagement with the trigger 294 when the mesh cartridge is loaded onto the device 282).

The introducer 284 and the anchor introducer cartridge 286 are both interchangeable and attachable to the delivery device 282 and configured to rotate as the anchor advancer 296 is squeezed. Suitable attachment mechanisms include ball detent systems similar to socket wrench snap-on devices. In one embodiment, each of the introducer 284 and the anchor introducer cartridge 286 engage with a rod that extends from the delivery device 282 in a manner similar to how a cylinder is attached to a single action revolver. In one embodiment, the anchor cartridge 286 defines a plurality of cylinder bores 408, with each cylinder bore 408 retaining a deployable anchor 287.

In one embodiment, the anchor is provided as a blunt anchor 287a (FIG. 21B) and includes a suture line 410 trailing from a distal end of the anchor 287a and terminating in a needle 412. In one embodiment, the anchor is provided as an arrow-shaped tissue piercing anchor 287b (FIG. 21C) that includes the suture line 410 trailing from a distal end of the anchor 287b and terminating in the needle 412. It is to be understood that the anchor introducer cartridge 286 could be loaded with anchors all of the same style (for example the blunt anchors 287a, or the arrow-shaped anchors 287b). In any regard, activating the anchor advancer 296 ejects one of the anchors 287 and a proximal direction for engagement with tissue at the landmark of the patient. Thereafter, the needle 412 and the suture line 410 are employed to deliver the support material 40 to the landmark.

In one embodiment, the support material 40 is pre-shaped and sized to extend from, for example, the sacrospinous ligament posterior the patient to an anterior location within a pelvic floor of the patient to repair pelvic organ prolapse. In one embodiment, the support 40 is a porous support in the form of a trapezoid having one pair of parallel sides and four fixation devices as shown in FIG. 2, with one fixation location 42 attached to the boundary 44 of the support 40 at each vertex of the trapezoid. In one embodiment, the fixation locations 42 on the reinforced boundary 44 are provided as grommet holes that are sized and configured to receive one of the anchors 287 and the suture line 410 trailing from the anchor.

In another embodiment, the surgical staff places one of the anchors 287 through a first portion of the reinforced boundary 44 to secure the support material 40 at the landmark, and a second one of the anchors 287 is placed through one of the fixation locations 42 in the reinforced boundary 44 to additionally secure the support material 40 at the landmark.

In one embodiment, the support material 40 is ejected from the introducer 284 by the system of gears 400/402 described above in FIG. 20. In one embodiment, the support material 40 is pneumatically ejected from introducer 284 through the use of compressed air or another air source as commonly provided in the surgical suite. In one embodiment, the barrel 390 of the delivery device 282 has an outside diameter of between 0.5-3 cm and is sized to receive a similarly sized mesh cartridge 284 or anchor introducer cartridge 286.

Figure 22:
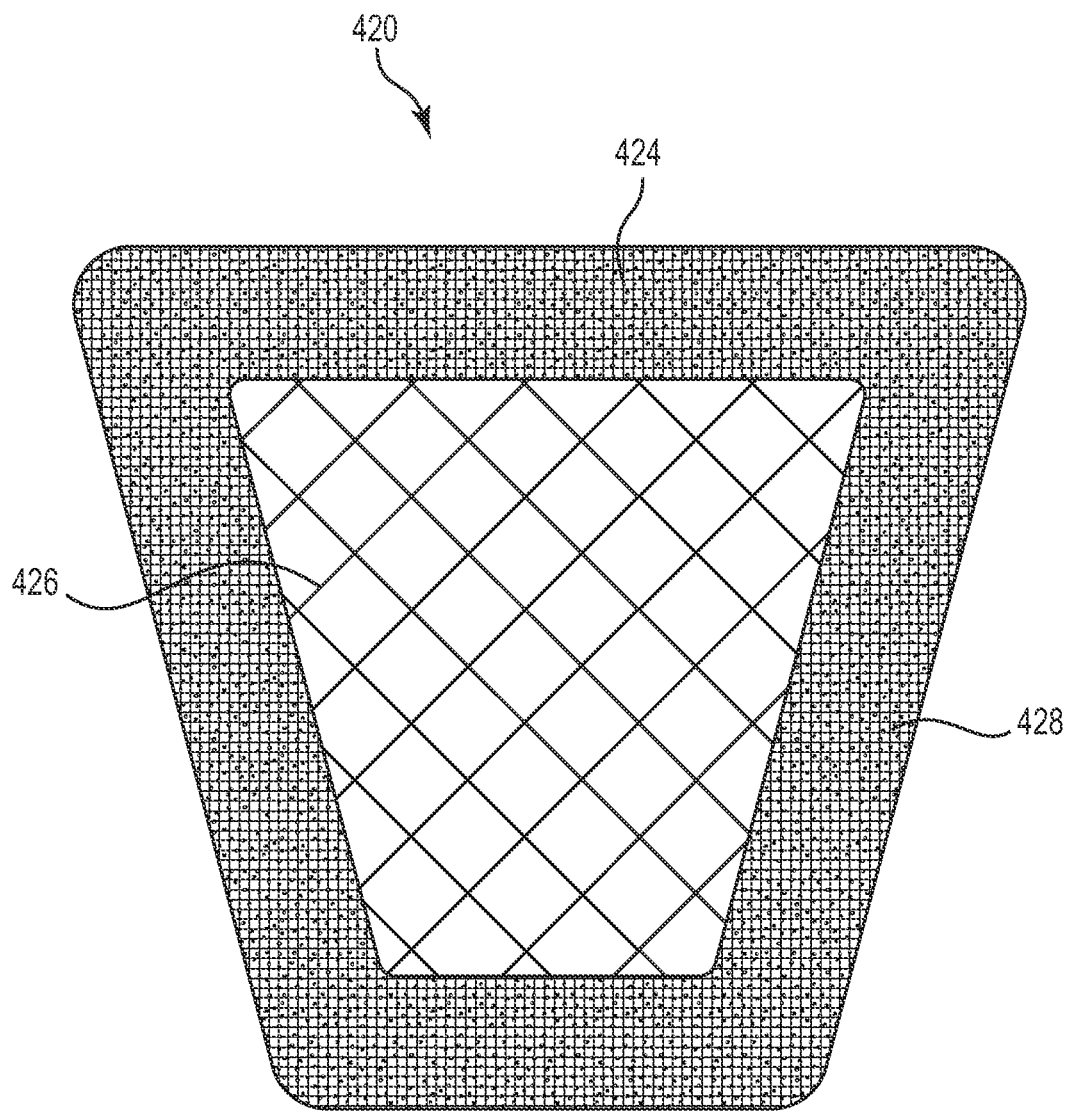
FIG. 22 is a top view of one embodiment of a support.

FIG. 22 is a top view of one embodiment of a support 420. The support 420 includes a reinforced border 424 placed in a central portion 426, and adhesive 428 disposed on the reinforced border 424. In one embodiment, the reinforced border 424 is placed around entire periphery of the central portion 426 and is provided with a pore size that is less (of pores are smaller) than the pore size of the central portion 426. The reinforced border 424 is configured to receive the suture line 410 attached to one of the anchors 287 deployed from the device 282, and when sutured to tissue, durably supports the placement of support 420 a patient.

The support 420 is affixed to the patient with sutures 410, with adhesive 428, or with sutures 410 and adhesive 428. In one embodiment, the support 420 is affixed with a bio-synthetic adhesive 428 derived from naturally-occurring compounds including, for example, various saltwater mollusks, invertebrates, and other adhesive-generating animals or those that are capable of creating other adhesive/structural materials.

The adhesive 428 can be pre-applied to the "anchoring" portion 424 of the support 420 with a release liner, and activated by, as examples: contact with moisture, contact with specific proteins located near or on the tissue, the application of a cross-linker by the surgeon, either by direct application or soaking in a solution. The adhesive 428 can also be applied in liquid form using an applicator instrument such as described in FIG. 5. The adhesive 428 can also be applied using a pre-moistened towelette that has the adhesive applied to it, and then wiped on to the attachment areas of the support 420 by the surgeon during the surgery.

The adhesive 428 once applied and activated, will in one embodiment have two stages of action. The first being an intra-operative stage, which will allow some adhesion to tissue but also allow the surgeon to remove and reposition the support 420. This stage will last for some set amount of time, for example two minutes. Once the surgeon either applies a certain force, or the implant is placed and not moved for a certain period of time (i.e., more than two minutes), the second stage will be activated, affixing the support 420 permanently in place. This stage will be completed during the time that the patient is recovering from surgery, for example. Cross-linking and complete adhesion will occur before the patient is upright.

The adhesive 428 is biodegradable in one embodiment. In this case, it will have a minimum time of 100% efficacy of 6 weeks, at which point it would start to break down and dissolve, eventually dissolving completely in the body.

As described above, the optic scope 292 allows the surgeon to visualize the placement of the anchors 287 and the support material 40 at the landmark. Typically, the placement of the support material 40 and the anchors 287 is delivered through a small access incision, for example 1-3 cm, formed in the patient (e.g., in the abdomen, in the perineum, or laparoscopically). The "narrow" barrel 390 of the delivery device 282 is introduced into the incision, allowing the surgeon to view the placement of the anchor 287 and support 40 at the landmark. In one embodiment, the barrel 390 of the delivery device 282 is sized to be introduced through the urethra of the patient and the optic scope 292 allows the surgeon to view the placement of the anchor 287 and support 40 at the landmark optically through the urethra.

The delivery device 282 is employed to fix the anchors 287 into the patient's tissue and to deliver the support material along the suture line 410 that is connected to each of the anchors. Embodiments provide the support material with an integrated tension adjustment mechanism that applies resistance to the suture line 410, which allows the surgeon to place and adjust the support material 40 accurately at a desired location.

Figure 23A:
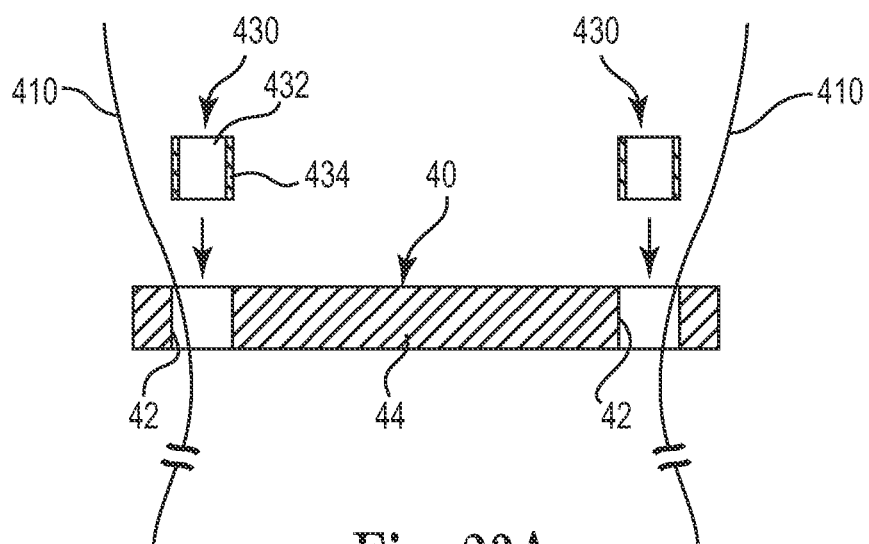
FIGS. 23A and 23B illustrate embodiments of tension devices integrated into the support material of FIG. 2.
Figure 23B:
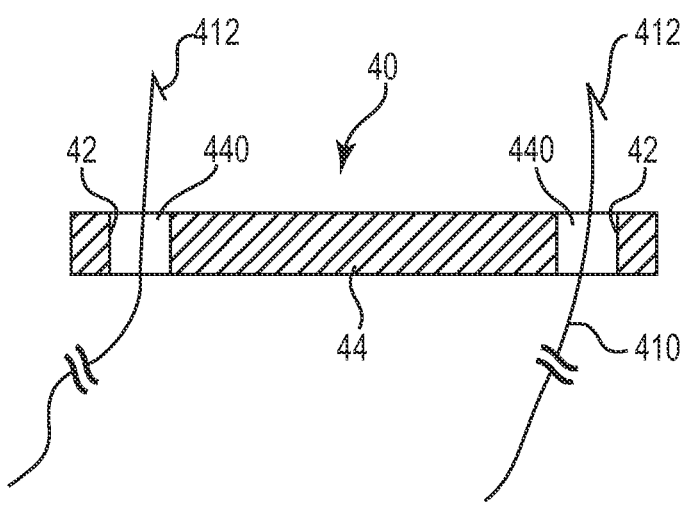

FIGS. 23A and 23B illustrate embodiments of tension devices integrated into the support material of FIG. 2, where the tension device is configured to apply a compression force to the suture line 410 attached to the support 40 that limits movement of the support 40 and the suture line 410.

FIG. 23A illustrates one embodiment of a tension device 430 insertable into the fixation device 42 of the support material 40 to adjustably fix the suture line 410 relative to the reinforced border 44. In one embodiment, the tension device 430 is provided as a plug that is sized to fit with the fixation device 42, and is provided to pinch or provide tension against the suture line 410 that is threaded through the grommet of the fixation device 42. In one embodiment, the tension device 430 includes a core 432 and a sleeve 434. In one embodiment, the core 432 is provided as a polymer that has a higher durometer than the sleeve 434, such that a sleeve 434 is softer than the core 432, which allows the sleeve 434 to compress against the suture line 410 and deliver sliding friction that limits the travel of the suture line 410. As an example, the core 432 is provided with a durometer of about 55-75 Shore A and the sleeve 434 is provided with a durometer of about 30-50 Shore A. In one embodiment, support 430 is provided with multiple fixation devices 42 (such as grommet holes) along with multiple tension devices 430 to plug the grommet holes 42.

During use, the surgeon deploys the anchors 287 into tissue and the suture 410 trails behind the anchor, for example outside of the patient's body. The surgeon directs the suture 410 through the grommet hole 42 and inserts the tension device 430 into the grommet hole 42 to press against and retain the suture 410. The tension device 430 allows the surgeon to selectively adjust the support 40 along the suture 410 until it is optimally placed. Thereafter, the tension device 430 resists movement of the suture 410 through the grommet hole 42 and the support 40 is retained as placed to allow tissue ingrowth leading to permanent fixation.

FIG. 23B illustrates one embodiment of another tension device 440 integrated into the support material 40 to adjustably fix the suture line 410 relative to the reinforced border 44. In one embodiment, the tension device 440 is molded into the fixation device 42 as a solid overlay or plug. During use, the suture line 410 is pushed through the tension device 440 (for example with needle 412) and the tension device 440 presses against the suture line 410 to hold in place. In one embodiment, the tension device 440 is molded as a silicone plug into the grommet hole 42 of the support 40 and has a thickness that is selected to provide frictional resistance to the suture 410. In one embodiment, the thickness of the tension device 440 is between about 0.5-2 mm and is fabricated from soft silicone material.

During use, the surgeon deploys the anchors 287 into tissue and the suture 410 trails behind the anchor, for example outside of the patient's body. The surgeon directs the suture 410 through the tension device 440, for example with a needle 412, and the tension device 440 frictionally retains the suture 410. The tension device 440 allows the surgeon to selectively adjust the support 40 along the suture 410 until it is optimally placed. Thereafter, the tension device 440 resists movement of the suture 410 through the support 40, and the support 40 is retained as placed to allow tissue ingrowth leading to permanent fixation.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of embodiments discussed herein. Therefore, it is intended that this invention be limited only by the claims and the equivalents thereof.

What is claimed is:

1. A system for repair of a prolapsed organ in a patient, the system comprising:
   a porous support;
   a deployment instrument having a handle extending from a barrel and a first trigger and a separate second trigger both offset from the handle;
   a support cartridge configured to be removably attachable to the barrel of the deployment instrument, the support cartridge defining a cavity that contains the support; and
   an anchor cartridge configured to be removably attachable to the barrel of the deployment instrument and configured to be interchangeable with the support cartridge, the anchor cartridge defining a plurality of cylinder bores, each cylinder bore retaining a deployable anchor;
   wherein the first trigger is operable to advance the support out of the support cartridge and into the patient after securing the support cartridge to the barrel and the second trigger is operable to advance one of the deployable anchors out of the anchor cartridge and into tissue of the patient after interchanging the support cartridge with the anchor cartridge by removing the support cartridge from the barrel and securing the anchor cartridge to the barrel.

2. The system of claim 1, wherein the barrel defines a bore that retains the support in operable engagement with the first trigger.

3. The system of claim 1, further comprising:
an optical scope associated with the barrel and configured to allow a user of the deployment instrument to visualize advancement of the support out of the barrel of the deployment instrument and into the patient.

4. The system of claim 1, wherein the support comprises a central portion provided with a first pore size and a boundary surrounding a perimeter of the central portion that is provided with a second pore size that is smaller than the first pore size.

5. The system of claim 4, wherein the central portion has a first density and the boundary has a second density that is greater than the first density.

6. The system of claim 4, wherein the central portion has a first strength and the boundary has a second strength that is greater than the first strength.

7. The system of claim 4, further comprising:
at least one fixation device attached to the boundary and provided to attach the support to tissue of the patient.

8. The system of claim 7, wherein the porous support comprises a trapezoid having one pair of parallel sides and four fixation devices, one fixation device attached to the boundary of the support at each vertex of the trapezoid.

9. The system of claim 4, further comprising a tension device integrated into the boundary of the support, the tension device configured to apply a compression force to a suture line attached to the support that limits movement of the suture line.

10. The system of claim 1, wherein the barrel of the deployment instrument includes a recessed locking latch to which the anchor cartridge is removably attachable and to which the support cartridge is removably attachable separate from the anchor cartridge.

11. The system of claim 1, wherein the support cartridge is attachable to the distal end of the deployment instrument to define a first barrel of the system and the anchor cartridge is separately attachable from the support cartridge to the distal end of the deployment system to define a second barrel of the system.

12. The system of claim 1, wherein the deployment instrument includes a longitudinally extending pin, and the support cartridge and the anchor cartridge are each separately configured to engage with the pin and revolve about the pin.

13. A system for repair of a prolapsed organ in a patient, the system comprising:
a porous support;
a deployment instrument having a handle extending from a barrel and a trigger offset from the handle;
a support cartridge configured to be removably attachable to the barrel of the deployment instrument, the support cartridge defining a cavity that contains the support in operable engagement with the trigger; and
an anchor cartridge configured to be removably attachable to the barrel of the deployment instrument and configured to be interchangeable with the support cartridge, the anchor cartridge defining a plurality of cylinder bores, each cylinder bore retaining a deployable anchor;
wherein the trigger is operable to advance one of the deployable anchors out of the anchor cartridge and into tissue of the patient after securing the anchor cartridge to the barrel and to advance the support out of the support cartridge and into engagement with the anchor advanced into the tissue of the patient after interchanging the anchor cartridge with the support cartridge by removing the anchor cartridge from the barrel and securing the support cartridge to the barrel.

14. A system for repair of a prolapsed organ in a patient, the system comprising:
a porous support;
a deployment instrument having a handle extending from a barrel and a trigger offset from the handle;
means for containing the support in operable engagement with the trigger; and
means for containing a tissue anchor in operable engagement with the trigger;
wherein the means for containing the support in operable engagement with the trigger and the means for containing a tissue anchor in operable engagement with the trigger are interchangeably connectable to the deployment instrument and the trigger is operable to advance the tissue anchor into tissue of the patient after securing the anchor cartridge to the barrel and to advance the support into engagement with the anchor advanced into the tissue of the patient after interchanging the support cartridge with the anchor cartridge by removing the support cartridge from the barrel and securing the anchor cartridge to the barrel.

15. A method of repairing a prolapsed organ in a patient, the method comprising:
loading a tissue anchor into a deployment instrument by attaching an anchor cartridge to a barrel of the deployment instrument, the anchor cartridge providing a plurality of bores and each bore retaining a tissue anchor;
discharging the tissue anchor from the deployment instrument into tissue of the patient;
loading a support fabric into the deployment instrument by removing the anchor cartridge from the barrel of the deployment instrument and attaching a support cartridge to the barrel of the deployment instrument, the support cartridge containing the support fabric; and
discharging the support fabric from the deployment instrument and engaging the support fabric with the tissue anchor.

16. The method of claim 15, wherein discharging the tissue anchor from the deployment instrument into tissue of the patient comprises:
discharging a first tissue anchor from a first bore of the anchor cartridge;
rotating the anchor cartridge relative to the barrel of the deployment instrument and discharging a second tissue anchor from a second bore of the anchor cartridge.

17. The method of claim 15, wherein discharging the tissue anchor from the deployment instrument into tissue of the patient comprises attaching the tissue anchor into the tissue of the patient and providing a suture line trailing from the tissue anchor away from the tissue of the patient.

18. The method of claim 17, further comprising:
advancing a support mesh along the suture line trailing from the tissue anchor to a location adjacent to the tissue of the patient.

19. The method of claim 15, wherein engaging the support fabric with the tissue anchor comprises attaching a boundary of the support fabric to tissue of the patient and supporting the prolapsed organ of the patient with a central portion of the support fabric, the boundary of the support fabric reinforced relative to the central portion to have a porosity that is less than a porosity of the central portion.

20. The method of claim 15, further comprising a step of receiving the anchor cartridge loaded with the plurality of tissue anchors prior to attaching the anchor cartridge to the deployment instrument, and a step of receiving the support cartridge loaded with the support fabric prior to attaching the support cartridge to the deployment instrument.

21. The method of claim 15, further comprising a first step of receiving a kit including the deployment instrument, the anchor cartridge and the support cartridge, wherein the anchor cartridge is attached to the deployment instrument when the kit is received.

* * * * *